US011305077B2

(12) United States Patent
Bogan et al.

(10) Patent No.: US 11,305,077 B2
(45) Date of Patent: *Apr. 19, 2022

(54) THERAPEUTIC DEVICE FOR TREATMENT OF CONDITIONS RELATING TO THE SINUSES, NASAL CAVITIES, EAR, NOSE AND THROAT

(71) Applicant: Healthy Humming, LLC, Columbia, SC (US)

(72) Inventors: Richard K. Bogan, Johns Island, SC (US); David J. Lewis, Columbia, SC (US); Caleb Pinckney, Chapin, SC (US); David Bonner, Knoxville, TN (US); Michael Maloney, Caledon East (CA)

(73) Assignee: Healthy Humming, LLC, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/517,125

(22) Filed: Nov. 2, 2021

(65) Prior Publication Data
US 2022/0054779 A1 Feb. 24, 2022

Related U.S. Application Data

(63) Continuation-in-part of application No. 16/405,038, filed on May 7, 2019, now Pat. No. 11,213,641,
(Continued)

(51) Int. Cl.
*A61H 23/00* (2006.01)
*A61H 1/00* (2006.01)
(Continued)

(52) U.S. Cl.
CPC .......... *A61M 16/0006* (2014.02); *A61H 1/00* (2013.01); *A61H 9/0007* (2013.01);
(Continued)

(58) Field of Classification Search
CPC .......... A61M 16/0006; A61M 15/0013; A61M 15/0098; A61M 15/0085; A61M 15/0086;
(Continued)

(56) References Cited

U.S. PATENT DOCUMENTS

| 2,918,917 A | * | 12/1959 | Emerson | ........... A61M 16/0009 |
| | | | | 128/205.19 |
| 3,812,853 A | | 5/1974 | Crain | |

(Continued)

FOREIGN PATENT DOCUMENTS

| CN | 86200594 U | 12/1986 |
| CN | 2363679 Y | 2/2000 |

(Continued)

OTHER PUBLICATIONS

Weitzberg, E/Lundberg, Jon O.N. Humming Greatly Increases Nasal Nitric Oxide. Am J. Respir Crit Care Med., vol. 166. pp. 144-145 (2002).

(Continued)

*Primary Examiner* — Tu A Vo
(74) *Attorney, Agent, or Firm* — Haynsworth Sinkler Boyd, P.A.

(57) ABSTRACT

A therapeutic device for treating one or more conditions associated with a user's nasal cavities, sinuses, and/or ear canals includes a housing having an opening, an acoustic vibrator within the housing that is operable to provide an acoustic vibration to the user, a fan within the housing that is operable to provide a pressure to the user and a power supply that provides power to the acoustic vibrator and the fan. A mask is connected to the housing at the opening and includes a nasal interface appliable around the nose of the user, a nasal chamber in which the user's nostrils are located and an aperture through which the fan delivers the pressure.

20 Claims, 13 Drawing Sheets

Related U.S. Application Data which is a continuation-in-part of application No. 15/891,019, filed on Feb. 7, 2018, now abandoned, which is a continuation-in-part of application No. PCT/US2017/051484, filed on Sep. 14, 2017.

(60) Provisional application No. 62/394,355, filed on Sep. 14, 2016.

(51) Int. Cl.
| | |
|---|---|
| *A61H 9/00* | (2006.01) |
| *A61M 16/06* | (2006.01) |
| *A61M 16/20* | (2006.01) |
| *A61M 16/00* | (2006.01) |
| *A61H 23/02* | (2006.01) |
| *A61M 15/00* | (2006.01) |
| *A61M 15/08* | (2006.01) |
| *A61M 16/16* | (2006.01) |

(52) U.S. Cl.
CPC ....... *A61H 23/004* (2013.01); *A61H 23/0236* (2013.01); *A61H 23/0245* (2013.01); *A61M 15/0013* (2014.02); *A61M 15/0085* (2013.01); *A61M 15/0086* (2013.01); *A61M 15/0098* (2014.02); *A61M 15/08* (2013.01); *A61M 16/0072* (2013.01); *A61M 16/06* (2013.01); *A61M 16/0666* (2013.01); *A61H 2201/1238* (2013.01); *A61H 2201/5025* (2013.01); *A61H 2205/023* (2013.01); *A61H 2205/027* (2013.01); *A61M 16/16* (2013.01); *A61M 2202/0208* (2013.01); *A61M 2202/0216* (2013.01); *A61M 2202/0225* (2013.01); *A61M 2202/0266* (2013.01); *A61M 2205/505* (2013.01); *A61M 2205/8206* (2013.01); *A61M 2210/0618* (2013.01); *A61M 2210/0662* (2013.01); *A61M 2210/0681* (2013.01)

(58) Field of Classification Search
CPC .... A61M 15/08; A61M 16/06; A61M 16/208; A61M 15/00; A61M 16/16; A61M 2202/0208; A61M 2202/0216; A61M 2202/0225; A61M 2202/0266; A61M 2205/505; A61M 2210/0618; A61M 2210/0662; A61M 2210/0681; A61H 1/00; A61H 23/00; A61H 23/0236; A61H 23/0245; A61H 23/04; A61H 2201/1238; A61H 2201/5025; A61H 2205/023; A61H 2205/027; A61H 2023/002; A61H 23/004; A61H 23/006; A61H 23/02; A61H 2023/0209; A61H 23/0218; A61H 2023/0227; A61H 23/0254; A61H 23/0263; A61H 2023/0272; A61H 2023/0281; A61H 2023/029; A61H 2023/045; A61H 23/06
See application file for complete search history.

(56) References Cited

U.S. PATENT DOCUMENTS

| | | | | |
|---|---|---|---|---|
| 4,026,284 | A | * | 5/1977 | Boehringer ......... A61M 16/009 128/205.24 |
| 4,369,777 | A | | 1/1983 | Lwoff et al. |
| 4,401,114 | A | | 8/1983 | Lwoff et al. |
| 4,403,616 | A | * | 9/1983 | King ..................... A63B 23/18 482/13 |
| 4,813,403 | A | * | 3/1989 | Endo .................. A61H 23/0236 601/46 |
| 5,018,517 | A | | 5/1991 | Liardet |
| 5,193,529 | A | | 3/1993 | Labaere |
| 5,451,190 | A | * | 9/1995 | Liardet ................. A63B 23/18 128/200.24 |
| 5,829,429 | A | * | 11/1998 | Hughes ................ A61M 16/00 128/200.24 |
| 6,058,932 | A | * | 5/2000 | Hughes ................ A61M 16/00 128/200.24 |
| 6,237,594 | B1 | | 5/2001 | Davenport |
| 6,520,931 | B2 | | 2/2003 | Suh |
| 6,561,188 | B1 | | 5/2003 | Ellis |
| 7,980,247 | B2 | | 7/2011 | Boehm et al. |
| 8,006,698 | B2 | | 8/2011 | Boehm et al. |
| 8,056,558 | B2 | | 11/2011 | Bracken |
| 8,398,580 | B2 | | 3/2013 | Rasor et al. |
| 8,424,527 | B1 | | 4/2013 | Kayyali |
| 8,485,179 | B1 | * | 7/2013 | Meyer .................. A61M 16/14 128/200.24 |
| 8,539,951 | B1 | * | 9/2013 | Meyer ............... A61M 16/0006 128/205.24 |
| 8,844,530 | B2 | | 9/2014 | Bimkrant |
| 8,899,230 | B2 | | 12/2014 | Immel |
| 2005/0139221 | A1 | | 6/2005 | Duncan |
| 2006/0207599 | A1 | | 9/2006 | Busch et al. |
| 2006/0260609 | A1 | | 11/2006 | Bruening |
| 2007/0113843 | A1 | * | 5/2007 | Hughes ............... A61M 16/208 128/200.24 |
| 2008/0200848 | A1 | | 8/2008 | Avni |
| 2008/0289629 | A1 | | 11/2008 | Djupesland et al. |
| 2010/0170513 | A1 | | 7/2010 | Bowditch et al. |
| 2010/0274164 | A1 | | 10/2010 | Juto |
| 2011/0120456 | A1 | | 5/2011 | Immel |
| 2011/0201977 | A1 | | 8/2011 | Tass |
| 2011/0307039 | A1 | | 12/2011 | Cornell |
| 2012/0085344 | A1 | * | 4/2012 | Luber ............... A61M 15/0085 128/200.16 |
| 2012/0095374 | A1 | | 4/2012 | Hughes |
| 2012/0167892 | A1 | | 7/2012 | Matula, Jr. |
| 2013/0012869 | A1 | * | 1/2013 | Cha ..................... A61M 3/0258 604/28 |
| 2013/0158451 | A1 | | 6/2013 | Juto et al. |
| 2013/0158452 | A1 | | 6/2013 | Juto et al. |
| 2013/0184619 | A1 | | 7/2013 | Von Hollen |
| 2013/0345606 | A1 | | 12/2013 | Ehrenreich et al. |
| 2014/0096773 | A1 | | 4/2014 | Amarasinghe |
| 2014/0150801 | A1 | * | 6/2014 | Rusher ................ A63B 21/0088 128/207.16 |
| 2014/0261425 | A1 | | 9/2014 | Connor |
| 2015/0053201 | A1 | | 2/2015 | Djupesland et al. |
| 2015/0073316 | A1 | | 3/2015 | Bende |
| 2015/0297845 | A1 | | 10/2015 | Shahaf et al. |
| 2015/0306324 | A1 | | 10/2015 | Ayon et al. |
| 2015/0374939 | A1 | * | 12/2015 | Meyer .................. A61M 16/021 128/200.23 |
| 2016/0045693 | A1 | | 2/2016 | Librett et al. |
| 2016/0082214 | A1 | | 3/2016 | Barlow et al. |
| 2016/0121062 | A1 | * | 5/2016 | Davenport ............. A61H 23/02 601/47 |
| 2017/0157429 | A1 | * | 6/2017 | Deehr ................ A61H 23/0245 |
| 2017/0157435 | A1 | | 6/2017 | Choi |
| 2017/0224943 | A1 | | 8/2017 | Creusot et al. |
| 2018/0001065 | A1 | | 1/2018 | Chang et al. |
| 2018/0133102 | A1 | | 5/2018 | Owen |
| 2018/0185595 | A1 | | 7/2018 | Bogan et al. |

FOREIGN PATENT DOCUMENTS

| | | | |
|---|---|---|---|
| CN | 2566859 | Y | 8/2003 |
| CN | 2738819 | Y | 11/2005 |
| CN | 2834592 | Y | 11/2006 |
| CN | 201481939 | U | 5/2010 |
| CN | 203154277 | U | 8/2013 |
| CN | 204033952 | U | 12/2014 |
| CN | 205055166 | U | 3/2016 |
| EP | 1757321 | A3 | 11/2007 |
| FR | 2543442 | A1 | 10/1984 |
| KR | 20020000600 | A | 1/2002 |
| KR | 100387323 | B1 | 6/2003 |

(56) References Cited

FOREIGN PATENT DOCUMENTS

| | | |
|---|---|---|
| KR | 100720053 B1 | 5/2007 |
| KR | 101019957 B1 | 3/2011 |
| WO | 2011067752 A1 | 6/2011 |

OTHER PUBLICATIONS

Shusterman, D The Nasal Nitric Oxide Response to External Acoustic Energy: A Pilot Study of Sampling Dynamics. Sinusitis 2015, 1, pp. 13-23.

Maniscalco, M/Sofia, M/Weitzberg, E/Lundberg, J.O. Sounding Airflow Enhances Aerosol Delivery Into the Paranasal Sinuses. European Journal of Clinical Investigation (2006) 36, pp. 509-513.

Lundberg, Jon O. Nitric Oxide and the Paranasal Sinuses. The Anatomical Record, Record 291, pp. 1479-1484 (2008).

Written Opinion of the International Searching Authority regarding PCT/US2017/51484, dated Nov. 29, 2017, 8 pages, International Searching Authority, Alexandria, VA.

Notification of Transmittal of the International Search Report and the Written Opinion of the International Searching Authority, or the Declaration regarding PCT/US2017/51484, dated Nov. 29, 2017, 3 pages, International Searching Authority, Alexandria, VA.

M. Durand, S. Le Guellec, J. Pourchez, F. Dubois, G. Aubert, G. Chantrel, L. Vecellio, C. Hupin, R. De Gersem G. Reychler, L. Pitance, P. Diot and F. Jamar Sonic aerosol therapy to target maxillary sinuses. Europeans Annals of Otorhinolaryngology, Head and Neck diseases (2012) 129, pp. 244-250, http://www.sciencedirect.com/science/journal/18797296.

Amira El Merhie, Laurent Navarro, Xavier Delavenne, Lara Leclerc and Jérémie Pourchez A new Strategy to Improve Drug Delivery to the Maxillary Sinuses: The Frequency Sweep Acoustic Airflow. HAL Id: hal-01319445; https://hal.archives-ouvertes.fr/hal-01319445 (Submitted on May 20, 2016).

Laurent Vecellio, Sandrine Le Guellec and Gilles Chantrel Sonic Nebulisation in Rhinology. AeroDrug/DTF Medical, www.aerodrug.com.

510(k) Summary, submitted by Medical Acoustics, LLC for Lung Flute, Jun. 22, 2006.

510(k) Summary, submitted by Medical Acoustics, LLC for Lung Flute Therapeutic, Jan. 4, 2010.

510(k) Summary, submitted by Westmed, Inc. for Vibralung Acoustical Percussor, May 23, 2014.

Sanjay Sethi, M.D., Jane Maloney, R.N., Lori Grove, B.S. and Pamela K. Anderson R.N. Comparison of the Lung Flute with the Acapella in the Treatment of COPD with Chronic Bronchities. VA WNY Health Care System, Buffalo, NY and University at Buffalo, SUNY, Buffalo, NY.

\* cited by examiner

Section A-A

Section B-B

THERAPEUTIC DEVICE FOR TREATMENT OF CONDITIONS RELATING TO THE SINUSES, NASAL CAVITIES, EAR, NOSE AND THROAT

REFERENCE TO RELATED APPLICATIONS

This continuation in part application claims priority to U.S. patent application Ser. No. 16/405,038, filed on May 7, 2019, which claims priority to U.S. patent application Ser. No. 15/891,019 filed on Feb. 7, 2018, which claims priority to International Application No. PCT/US 17/51484 filed on Sep. 14, 2017, which claims priority to U.S. Provisional Patent Application No. 62/394,355 filed on Sep. 14, 2016. The entire contents of these applications are incorporated herein by reference.

BACKGROUND

Many individuals suffer from sinusitis, which is characterized by tippet airway mucosal edema, inflammation and obstruction. Normally, the sinuses are filled with air, but inflammation and edema cause obstructions, fluid (e.g., mucus, drainage, etc.) and/or infectious material (e.g., bacteria, viruses, etc.) to accumulate. Sinusitis causes many uncomfortable symptoms, including pain resulting from pressure in the sinus cavities, nasal mucus discharge, headaches, and many others. Accordingly, there is a need to treat sinusitis, including acute, subacute, recurrent and/or chronic sinusitis.

In addition, Eustachian equilibrium may be lost when a person encounters sudden changes in pressure, such as when an airplane takes off and/or lands, which causes the pressure in the ear canals to become unbalanced. There is a need to treat this loss of Eustachian equilibrium that results from sudden changes in pressure.

SUMMARY

According to an implementation, described herein, a therapeutic device for treating one or more conditions associated with a user's nasal cavities, sinuses, and/or ear canals, the therapeutic device may include a vibration generator configured to provide a vibration to a nasal interface of the user, the nasal interface located over a nose, around the nose or in the nose of the user. The therapeutic device may also include a gas module configured to provide a gas having a positive pressure to the user at a chamber and a seal configured to maintain the positive pressure at the chamber. The therapeutic device may also include a power module configured to provide power to the vibration generator to create the vibration and a housing which the user may bold and which is connected to the vibration generator, the gas module, and the power module. The therapeutic device may further include a user interface mourned to the housing and operable by the user to control one or more of the following functions of the therapeutic device: increase the positive pressure of the gas; decrease the positive pressure of the gas; modulate the positive pressure of the gas; increase the frequency of the modulation of the positive pressure of the gas, decrease the frequency of the modulation of the positive pressure of the gas: turn on the positive pressure of the gas; turn off the positive pressure of the gas; increase the vibration produced by the vibration generator; or decrease the vibration produced by the vibration generator. The gas module of the therapeutic device may serve as the vibration generator by modulating the positive pressure of the gas.

The therapeutic device may further include a medication module configured to provide a medication to the user and a user interface mounted to the housing and operable by the user to control one or more of the following functions of the therapeutic device; turn on the medication module to provide medication to the user; turn off the medication module to stop medication from being provided to the user; increase the amount of medication provided to the user via the medication module; or decrease the amount of medication provided to the user via the medication module. The therapeutic device may include a seal on the housing and/or a chamber locked within the housing. The therapeutic device may further include a nasal pillow extending from the housing and connected to the vibration generator. The seal may be located on the nasal pillow, and the chamber may be located within the nostril associated with the nasal pillow. The vibration may be delivered to the user via the nasal pillow, and the nasal pillow may further include ballast. The power module may provide power generated by the breath of the user or a crank operated by the user to the vibration generator to provide the vibration to the user. The power provided by the power module may be electrical power or rotational power. The therapeutic device may further include at least one of a temperature control module to warm the gas or a humidity control module to increase or decrease the humidity of the gas. The gas may correspond to one or more of: air, oxygen, nitrogen, helium, carbon dioxide, water vapor, exhaled breath of the user, or helox. The positive pressure of the gas may be from four to twenty-five centimeters of water or from four to ten centimeters of water. The therapeutic device may include a valve that prevents the positive pressure in the chamber from exceeding a threshold.

According to another implementation, described herein, a manually operated therapeutic device for treating one or more conditions associated with a user's nasal cavities, sinuses, and/or ear canals, may include a vibration generator configured to provide a vibration to a nasal interface of the user, the nasal interface being located over a nose, around the nose or in the nose of the user. The therapeutic device may fun her include a power module configured to provide power generated by the user to the vibration generator and a gas module configured to provide a gas having a positive pressure to the user at a chamber. The gas module may include a reservoir that may be filled by the exhaled breath of the user to provide the positive pressure of the gas. The therapeutic device may further include a seal configured to maintain the positive pressure at the chamber and a housing that the user may hold and that is connected to the seal, the vibration generator, the power module and the gas module. The power generated by the user may come from the exhaled breath of the user or a crank rotated by the user. The therapeutic device may include a cover.

According to another implementation, described herein, a method for treating one or more conditions associated with a user's nasal cavities, sinuses, and/or ear canals, may include providing a therapeutic device that includes a vibration generator configured to provide a vibration to a nasal pillow located at a nasal interface of the user, the nasal interface located in a nose of the user. The therapeutic device may further include a gas module configured to provide a gas having a positive pressure to the user at a chamber and a seal configured to maintain the positive pressure at the chamber. The method may further include operating the therapeutic device to provide the vibration to the nasal pillow and operating the therapeutic device to provide the gas to the chamber.

According to another implementation, described herein, a therapeutic device for treating one or more conditions associated with a user's nasal cavities, sinuses, and/or ear canals includes a vibration generator that includes an acoustic device configured to provide a sound. The therapeutic device further includes a seal that may be applied to a nasal interface of the user, the nasal interface being located around the nose and/or mouth of the user. The therapeutic device further includes a housing which the user may hold and which is connected to the vibration generator and the seal. The vibration generator may apply the sound to the nasal interface of the user when the seal is applied to the nasal interface of the user. The therapeutic device may further include an air-tight chamber formed within the housing when the seal is applied to the nasal interface of the user and a gas module connected to the housing and configured to provide a positive pressure in the air-tight chamber. The positive pressure may be generated by an exhaled breath of the user. The therapeutic device may further include a poppet valve that limits the positive pressure. The therapeutic device may further include a check valve that prevents a vacuum from being created in the air-tight chamber. The therapeutic device may further include a user interface that is operable by the user to control one or more of the following functions of the therapeutic device, turn the sound on; turn the sound off; increase a sound level produced by the vibration generator; decrease the sound level produced by the vibration generator; increase a frequency of the sound; or decrease the frequency of the sound. The therapeutic device may further include a power module. The power module may be located within the vibration generator. The vibration generator may include a signal source. The vibration generator may receive a signal from an external source, the signal being used by the acoustic device to generate the sound. The acoustic device may be a speaker, an electroacoustic transducer, a tone generator, a tone module, an ultrasonic generator, an ultra-low frequency generator, or a buzzer. The sound may resemble humming. The sound may have a frequency of from about 100 hertz to about 150 hertz. The sound may have a sound level of from about 20 decibels to about 100 decibels. The gas module may produce a vibration.

According to another implementation, described herein, a therapeutic device for treating one or more conditions associated with a user's nasal cavities, sinuses, and/or ear canals includes a vibration generator that includes an acoustic device that converts a signal to a sound. The signal is generated by the vibration generator or an external device. The therapeutic device further includes a housing that the user may hold and that is connected to the vibration generator. The housing is connectable to a nasal interface of the user to provide the sound to the nasal cavities, sinuses and/or ear canals of the user. The therapeutic device may further include a gas module that Is connected to the housing and powered by the exhaled breath of the user to provide a positive pressure to the user or to provide a vibration to the user.

According to another implementation, described herein, a method for treating one or more conditions associated with a user's nasal cavities, sinuses, and/or ear canals includes providing a therapeutic device including a vibration generator configured to provide a sound. The method further includes applying the therapeutic device to a nasal interface of the user. The method further includes operating the therapeutic device to apply the sound to the nasal interface of the user. The method may further include exhaling by the user to provide a positive pressure to the nasal interface of the user or to provide a vibration to the nasal interface of the user. The method may further include a sound that has a frequency of from about 100 hertz to about 150 hertz.

According to another implementation described herein, a therapeutic device for treating one or more conditions associated with a user's nasal cavities, sinuses, and/or ear canals includes a housing which the user may hold to apply the therapeutic device to the user, the housing including an inlet that allows air to enter the therapeutic device. The therapeutic device further includes an acoustic vibrator that is operable to provide an acoustic vibration to the user, the acoustic vibrator located within the housing. The therapeutic device further includes a power supply that provides power to the acoustic vibrator, the power supply located within the housing. A mask is connected to the housing and includes a nasal interface appliable around the nose of the user and a valve that is aligned with the inlet, the valve opening to allow the the user to breathe through the inlet and closing to prevent the user from exhaling through the inlet. The mask further includes a diaphragm opposite the nasal interface, the diaphragm being a closed end of the mask, and a nasal chamber extending from the nasal interface, the user's nostrils being located in the nasal chamber when the nasal interface is applied around the nose of the user. The acoustic vibrator provides the acoustic vibration directly to the nose of the user when the nasal interface is applied around the nose of the user and when the acoustic vibrator is operated to provide the acoustic vibration. The nasal interface may create a seal between the mask and the user when the nasal interface is applied around the nose of the user, the seal permitting pressure to be maintained in the nasal cavity. The mask may include a vent that is aligned with a mechanical vibrator, the mechanical vibrator creating a pressure in the nasal chamber or providing a mechanical vibration to the user when the seal is created between the user and the mask and when the user exhales into the nasal interface, the exhaled breath of the user being provided to the mechanical vibrator through the vent. The pressure may be determined by the weight of a ball bearing located within the mechanical vibrator, the vent aligned with the ball bearing. The ball bearing may oscillate to produce the mechanical vibration. The therapeutic device may farther include a second valve that aligns with a second inlet, the second valve located in mask opposite valve and the second inlet located in housing opposite inlet. The therapeutic device may further include a user interface operable by the user to deliver the sound to the user. The user interface may be a button. The acoustic vibration may have a frequency of from about 100 hertz to about 150 hertz. The acoustic vibrator may include an amplifier that provides a signal to a speaker, the signal used by the speaker to provide the acoustic vibration. The signal may be provided at a frequency above 20,000 hertz. The acoustic vibrator may include a button, the button operated by the user inter face to provide the acoustic vibration for a minimum amount of time. The mask may be removably connected to the housing. The valve may corresponds to a flap of material.

According to another implementation described herein, a mask for a therapeutic device includes a nasal interface appliable around a nose of a user and a valve that opens to allow a user to breathe through the valve when the nasal interface is applied to the user. The corresponds to a flap. The mask may further include a diaphragm opposite the nasal interface, the diaphragm being a closed end of the mask. The mask may further include a nasal cavity in which a user's nostrils are located when the nasal interface is applied around the nose of the user. The mask may be formed from silicone. That mask may be a one-piece design. The mask may include an inner portion that is insertable into the therapeutic device, the valve located on the inner portion. The mask may include a vent located on the inner portion, the vent corresponding to an aperture that allows the exhaled breath of the user to exit the nasal cavity when the nasal interface is applied to the user. The mask may include a recess into which the therapeutic device may be inserted, the inner portion located on one side of the recess. The recess may include a key that aligns the mask in the therapeutic device. A mask may include a second valve opposite the valve.

An example method for treating the nasal conditions of a user, described herein, includes providing a therapeutic device that produces an acoustic vibration, the therapeutic device includes a mask that includes a nasal interface appliable around the nose of the user and a nasal chamber extending from the nasal interface, a user's nostrils being insertable into the nasal chamber. The mask further includes a valve that opens to allow the user to inhale and closes to maintain a pressure in the nasal chamber. The therapeutic device further includes an acoustic vibrator that produces the acoustic vibration using a speaker and a housing connected to the mask, the acoustic vibrator located within the housing. The method further includes applying the nasal interface around the nose of the user and operating the therapeutic device to apply the sound to the nasal interface of the user. The method further includes exhaling by user to create a positive pressure in the nasal chamber. The therapeutic device may include a mechanical vibrator that produces a mechanical vibration when the user exhales. The sound may have a frequency of from about 100 hertz to about 150 hertz.

According to another implementation described herein, a therapeutic device for treating one or more conditions associated with a user's nasal cavities, sinuses, and/or ear canals, includes a housing including an opening, an acoustic vibrator that is operable to provide an acoustic vibration to the user, the acoustic vibrator located within the housing, and a fan that is operable to provide a pressure to the user, the fan located within the housing. A power supply provides power to the acoustic vibrator and the fan, the power supply is located within the housing. A mask is connected to the housing at the opening, the mask including a nasal interface appliable around the nose of the user, a nasal chamber extending from the nasal interface, the user's nostrils being located in the nasal chamber when the nasal interface is applied around the nose of the user, and an aperture, the fan delivering the pressure to the user through the aperture. Whereby, the acoustic vibrator provides the acoustic vibration directly to the nose of the user when the nasal interface is applied around the nose of the user and when the acoustic vibrator is operated to provide the acoustic vibration. Whereby, the fan provides the pressure directly to the nose of the user when the nasal interface is applied around the nose of the user and when the fan is operated to provide the pressure. The nasal interface may create a seal between the mask and the user when the nasal interface is applied around the nose of the user, the seal permitting pressure to be maintained in the nasal cavities. The power supply may be connected to a circuit board, and the circuit board operates the fan or the acoustic vibrator. The acoustic vibration may have a frequency of from 100 hertz to 150 hertz. The mask may be removably connected to the housing.

According to another implementation described herein, a a therapeutic device for treating one or more conditions associated with a user's nasal cavities, sinuses, and/or ear canals, includes a housing including an opening and an orifice, an acoustic vibrator that is operable to provide an acoustic vibration to the user, the acoustic vibrator located within the housing and a positive pressure unit that provides a pressure to the user that is generated by exhaled breath of the user. The positive pressure unit is connected to the housing proximate the orifice such that the exhaled breath of the user enters the positive pressure unit through the orifice. A power supply that provides power to the acoustic vibrator is located within the housing. A mask is connected to the housing at the opening, the mask including a nasal interface appliable around the nose of the user and a nasal chamber extending from the nasal interface, the user's nostrils being located in the nasal chamber when the nasal interface is applied around the nose of the user. Whereby, the acoustic vibrator provides the acoustic vibration directly to the nose of the user when the nasal interface is applied around the nose of the user and when the acoustic vibrator is operated to provide the acoustic vibration. Whereby, the positive pressure unit provides the pressure directly to the nose of the user when the nasal interface is applied around the nose of the user and the user exhales into the mask. The positive pressure unit may include a first chamber and a second chamber, the first chamber including a restrictor and the second chamber including a vane that is connected to the restrictor via a shaft. The restrictor may have an offset connection to the shaft. The restrictor and vane may be offset by an angle of between 45 degrees and 90 degrees. The restrictor and vane may be operable from a first position to a second position. The exhaled breath of the user may exit the second chamber through a first exit and second exit when the restrictor and vane are between the first position and the second position. The exhaled breath of the user may exit the second chamber through only a first exit when the restrictor and vane are in the first position. The positive pressure unit may include a flexible nozzle, the flexible nozzle including a pair of nozzle members. The positive pressure unit may include a fan that is powered by the exhaled breath of the user. The positive pressure unit may include a piston that is connected to a spring, the piston operable to an open position when the exhaled breath of the user creates a force that is stronger than a spring force generated by the spring. The positive pressure unit may include a piston that is connected to a motor, the motor operable to move the piston from a first position, in which the exhaled breath of the user is restricted from exiting the positive pressure unit by the piston, to a second piston position, in which the exhaled breath of the user is not restricted from exiting the positive pressure unit by the piston. The mask may be removably connected to the housing. The mask may include a vent, the vent aligned with the orifice. The motor may be connected to the power supply. The acoustic vibration may have a frequency of from 100 hertz to 150 hertz.

DETAILED DESCRIPTION

The apparatus, systems, methods, technologies and/or techniques (hereinafter "technology") described herein may provide a therapeutic device for the treatment of sinus conditions as well as methods by which users use the therapeutic device to treat sinusitis, and various other ailments of the sinuses, nasal cavities, ear, nose throat, etc. The technology may be described in FIGS. 1-7I. FIGS. 1-7I are attached hereto and incorporated herein by reference. The following detailed description refers to the accompanying FIGS. 1-7I. The same reference numbers in different figures may identify the same or similar elements. The embodiments depicted in FIGS. 1-7I are example embodiments, but the present technology may be embodied in many different embodiments.

Figure 1:
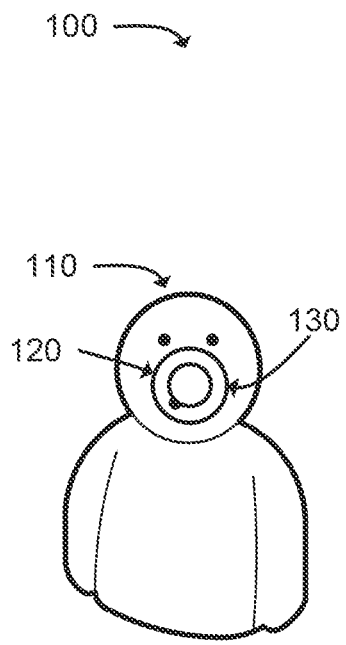
FIG. 1 represents an example environment in which the technology, described herein, may be implemented.

FIG. 1 depicts a non-limiting example environment in which the technology described herein may be implemented. As shown in FIG. 1, environment 100 may include a user 110, who may apply a therapeutic device 120 to form a seal 130 at around the nasal passages (covered by the therapeutic device 120 in FIG. 1) of the user. The user 110 may position the therapeutic device 120 by placing the therapeutic device 120 on, over, around or within the nostrils, nose, mouth, and/or face of a user. The seal may form a chamber associated with the nasal passages of a user 110, which chamber may be substantially air-tight and/or water-tight. The seal 130 may maintain a pressure within a chamber, may prevent or limit an amount of gas from entering and/or escaping the therapeutic device into the environment and/or may ensure that the user inhales some or all of the gas/medication/etc. being provided by the therapeutic device (e.g. via the chamber). The user 110 may suffer from one or more sinus conditions (e.g. mucus, drainage, infection, inflammation, pressure imbalance in sinuses and/or ear canals, etc.) that may be treated by therapeutic device 120. The seal may be located in the nasal passages, outside of the nasal passages, on the face around the nasal passages (as shown in FIG. 1), around the mouth and/or nose, etc. The therapeutic device may include a gas module (which may further including temperature and humidity controls), a vibration generator, a power module, a medication module, a valve, nasal pillows, and/or ballast for the purpose of treating sinus conditions as further described herein. The components illustrated in FIG. 1 are provided for explanatory purposes only, and the disclosure herein is not intended to be limited to the components provided therein. There may be additional components, fewer components, different components, and/or differently arranged components that illustrated in FIG. 1. Also, in some implementations, one or more of the components/modules of the therapeutic device of FIG. 1 may perform one or mote functions described as being performed by another one or more of the components/modules of the therapeutic device of FIG. 1. Further, the therapeutic device 120 of FIG. 1 is depicted as a device having a single-body construction. The therapeutic device may be formed as a single component and/or multiple components in a variety of structural designs and/or arrangements. FIG. 1 depicts an example environment 100 in which the technology may be implemented. Sample embodiments employing the technology are further described below.

Figure 2:
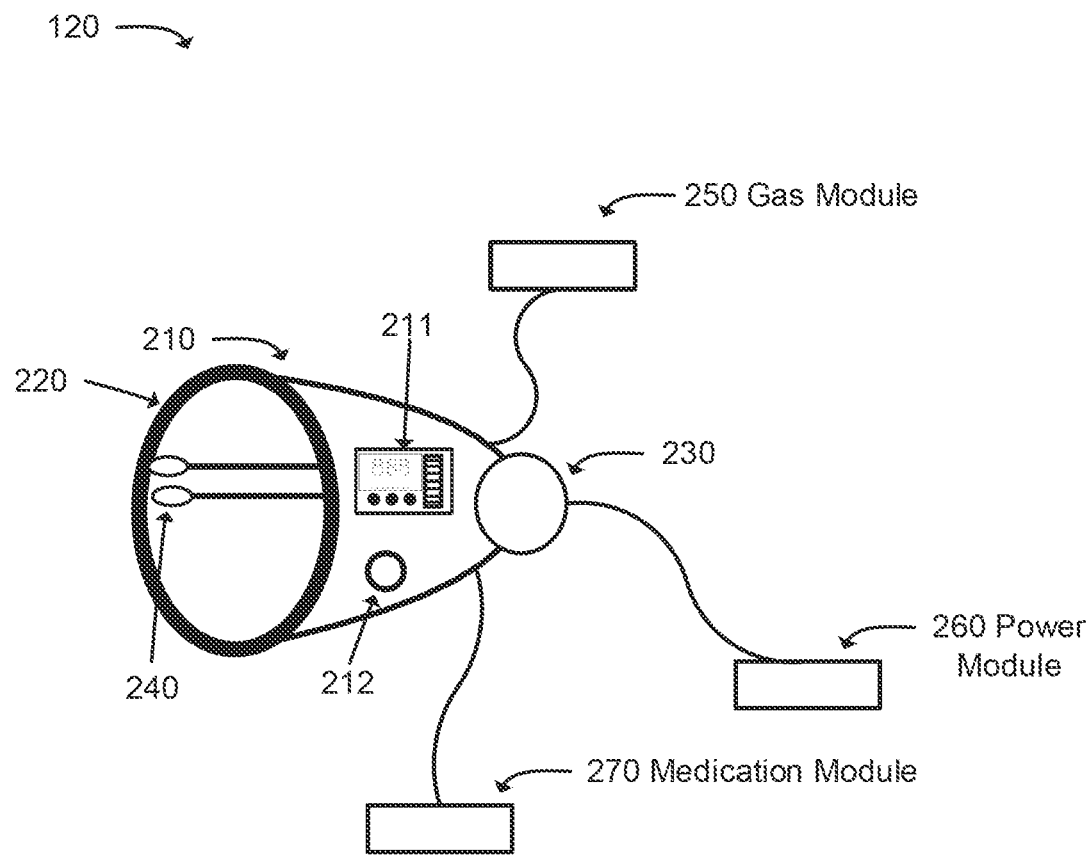
FIG. 2 represents a non-limiting example embodiment of the therapeutic device of FIG. 1.

FIG. 2 depicts an example embodiment of the therapeutic device 120 of FIG. 1. As shown in FIG. 2, therapeutic device 120 may include a housing 210 having a user interface 211, a valve 212, a seal 220, a vibration generator 230, nasal pillows 240, a gas module 250, a power source 200 and a medication module 270. The components illustrated in FIG. 2 are provided for explanatory purposes only, and the disclosure herein is not intended to be limited to, or to require, the components provided therein. There may be additional components, fewer components, different components, and/or differently arranged components than illustrated in FIG. 2. Also, in some implementations, one or more of the components/modules of the therapeutic device of FIG. 2 may perform one or more functions described as being performed by another one or more of the components/modules of the therapeutic device of FIG. 2. For example, and not limitation, the functions of vibration generator 230 may be provided by gas module 250 and/or power source 260.

The therapeutic device may include one or more modules that can impart a controlled amount of vibration to the user, via the nasal interface, in a manner that stimulates the nasal and sinus cavities of the user and/or relieves conditions related to the sinuses, nasal cavities, ears, nose and/or throat. The therapeutic device may also, or alternatively, include one or more modules that may provide a gas to a user, via the nasal interface, in a manner that stimulates the nasal and sinus cavities of the user and/or relieves conditions related to the sinuses, nasal cavities, ears, nose and/or throat. The therapeutic device may also, or alternatively, include one or more modules to control the temperature and/or humidity level of lire gas, and/or combine a controlled amount of medication (e.g., in liquid and or pow der form) with the gas. The therapeutic device may include a power module that stores power (e.g., a battery, battery pack, etc.) and/or receives power (e.g., a power supply that receives and/or controls power from an alternating current source), and/or can be manually powered by the user (e.g., by inhaling, exhaling, or some other means of manual power).

Housing 210 may be held by the user when using therapeutic device 120 to treat a sinus condition. Additionally, or alternatively, housing 210 may provide a chamber (e.g. when seal 220 is applied to the nasal interface) that may store a gas at a pressure and/or a medication to be delivered to a user to treat one or more of the conditions described herein. Additionally, or alternatively, one or more of the components of therapeutic device 120 may be permanently and/or removably mounted, installed and/or attached to housing 210 so that therapeutic device 120 may be more compact, convenient and/or be a one-piece design. Housing 210 may enclose one or more of the modules, discussed herein. Housing 210 may include a user interface 211 formed by one or more buttons, levers, displays, touch screens, dials, etc. with which the user may interact to control the therapeutic device (e.g. control vibration; control gas pressure, temperature, flow and/or humidity; medication delivery, etc.). Additionally, or alternatively, user interface 211 may be placed on any other component of therapeutic device 120, including the vibration generator 230, one of the modules, etc. User interface 211 may be a single unit, as displayed in FIG. 2, or may composed of separate components in different locations (e.g. the on/off switch in one location, and controls that adjust vibrations, etc., in another location) on therapeutic device 120. The user interface 211 may include a power switch, one or more buttons or user interfaces to control the settings associated with the modules described herein such as, for example, gas pressure, dosage, vibration level, vibration frequency, temperature, humidity, etc. The user interface may include a display, which may present information that identifies parameters associated with the modules described herein, such as charge level, gas level, pressure level, medication level, moisture level, vibration level, vibration frequency, temperature, etc.

Housing 210 may further include a valve 212, which may regulate the pressure and/or flow of gas into and/or from a chamber associated with housing 210. For example, and not limitation, valve 212 may correspond to a poppet valve, which may prevent the pressure within the chamber from exceeding a certain threshold associated with an opening pressure of the poppet valve. Additionally, or alternatively, valve 212 may correspond to a check valve, which may prevent a vacuum and/or pressure below ambient pressure from being created (e.g. when the user inhales) within chamber. Additionally, or alternatively, valve may correspond to a pressure regulation and/or flow regulation valve, which may limit the pressure within the chamber and/or the flow rate of a gas into and/or from the chamber.

Housing 210 may be formed from a material or materials of sufficient strength and rigidity (e.g. a polymer, a metal alloy, fiberglass, composite, etc.) to support the static and/or dynamic loads (e.g. forces, torques, tensions, compressions, stresses, strains, etc.) imparted on the housing 210 by the components of therapeutic device 120 (such as when they are installed on housing, apply pressure to housing, etc.), to support the handling of therapeutic device by the user, to support the pressures and or vibrations imparted to the housing 120 by the user and/or the components of the therapeutic device 120. Seal 220 may be the interface between therapeutic device 120 and the user, so the treatments (e.g. vibrations, pressures, medications, etc.), described herein, may be provided via seal 220 (e.g. vibrations passing through seal 220, pressure passing to user as a result of seal 220, etc.).

Seal 220 may be separate component that is permanently and/or removably attached to housing 210, nasal pillows 240 and/or some other portion of therapeutic device 120 that may create a chamber at the nasal interface of a user. A user may apply the seal 220 (e.g. by grasping housing and pressing seal around a nasal interface) to the user to form a chamber within which a gas (e.g. a pressurized gas, a therapeutic gas, etc.), medication, humidity, etc. may reside prior to being inhaled by the user. Seal 220 may be completely and/or partially air-tight. In the embodiment depicted in FIG. 2, seal 220 is located on a surface of housing 210 that cranes in contact with the face of the user. Additionally, or alternatively, seal 220 may be placed in other locations, such as nasal pillows 240. As depicted in FIG. 1, seal 220 may be formed in a shape (e.g., a mask, cover, etc.) that can fit over or around the nose of the user and/or the nose and mouth of the user. In this example, seal 220 may enable a positive pressure (e.g. above ambient pressure) to be created, controlled and/or maintained within a chamber (e.g. volume inside of the housing 210, etc.) when a gas is provided to the user by the therapeutic device 120. As further discussed herein, the pressure may be constant, modulated, may cause a vibration, etc. Additionally, or alternatively, therapeutic device 120 may provide a treatment (e.g. vibration, humidity, medication, temperature controlled gasses and/or medications, etc.) from one or more of the modules to the user via seal 220.

Seal 220 may be formed from a material or materials of sufficient strength and rigidity (e.g. polymers, rubbers, metals, etc.) to support the static and or dynamic loads (e.g. forces, torques, tensions, compressions, stresses, strains, etc.) imparted on the seal by other components of therapeutic device 120. For example, and not limitation, seal 220 may support vibration loads associated with pressure variation and/or a vibration generation device, may support pressure loads associated with the application of a pressure to the user. Additionally or alternatively, seal 220 may be formed from a material or materials of sufficient flexibility and resilience to be compressed by a user (such as when forming a seal at and/or around the nasal interface) and/or to be comfortably used by the user. For example, seal 220 may be formed from a gasket-like material which may be comfortable to the user and/or may maintain pressure within a chamber formed by the seal 220. Seal 220 may be removable to allow seal 220 to be cleaned and/or replaced.

Vibration generator 230 may provide mechanical vibrations to the user via the nasal interface (e.g. at seal 220, nasal pillows 240, etc.) Vibration generator 230 may contain one or more mechanical vibration-generating components (e.g., offset weight devices, cam-driven devices, etc.). For example, vibration generator may include one or more electrically driven vibration components, including, but not limited to, an eccentric rotating mass motor, an offset weight motor, a linear resonant actuator, a piezoelectric bender, etc. Additionally, or alternatively, the vibration generator may be mechanically driven. For example, the user may power a vibration device by breathing into the nasal interface. By inhaling and/or exhaling, the user may rotate a set of blades (e.g., a rotor blade, turbine blade, fan blade, etc.) that may be attached to a shaft associated with a mass that is offset from the center of the shaft. As the shaft rotates, the offset weight is rotated which creates a centrifugal force that is applied to the user when, for instance, the shaft is connected to (e.g. the shaft is allowed to rotate in a bearing and transfer the vibration forces, etc.) the nasal interface (e.g. connected to a member associated with nasal pillows 240, seal 220, etc.) Additionally, or alternatively, the user may exhale to fill a reservoir (e.g. such as a reservoir located within gas module 250) with exhaled breath (e.g. through a check valve that allows exhaled air to enter but not escape, etc.), and the pressure created and/or stored within the reservoir may be used (e.g. when another valve is operated, such as controlled by user interface 211, to allow gas to escape the reservoir, etc.) to rotate the set of blades to rotate the shaft that generates the vibration. Additionally, or alternatively, the user may manually operate a shaft (e.g., by operating a crank, etc.) to create vibrations, such as in the ways described herein. The scope of the present disclosure is not limited to the foregoing examples of vibration generation. Any type of known vibration device may be used. For example, an internal mass may be attached to a spring that may be depressed by a shaft that rides along a cam, which may be connected to a shaft that is driven by the user (e.g., the user's breath, by hand, etc.). Transferring the vibrations to the user via a nasal interface may stimulate the nasal and/or sinus cavities in a manner that breaks up and/or loosens liquid, mucus, solids and/or an obstruction within the nasal and/or sinus cavities of the user. Such stimulation may promote drainage of the nasal and/or sinus cavities. Additionally, or alternatively, the vibrations may open the ear canal to relieve pressure from the ear drum, which may be created by an infection, mucus, and/or changes in pressure (e.g., taking off and/or landing in an airplane).

Additionally, or alternatively, vibration generator 230 may be acoustically driven. Vibration generator 230 may include one or more acoustic devices that generate an acoustic vibration and/or a sound (a "sound"). Acoustic device may correspond to any sound generation device, including, for instance, a speaker, an electroacoustic transducer, a tone generator, tone module, ultrasonic generator, ultra-low frequency generator, buzzer, etc. The acoustic device may receive a signal (e.g. electrical signal that is converted to a sound by acoustic device etc.) from power module 260 or some external device and use such signal to generate the sound. Additionally, or alternatively, vibration generator 230 may include a signal source. A user may control the vibration generator 230, such as via the user inter face 211, to adjust the sound (i.e. turn the sound on or off, increase the frequency of the sound, decrease the frequency of the sound, increase the sound level of the sound, decrease the sound level of the sound, increase sound pressure, decrease sound pressure, increase vibrations associated with the sound, decrease vibrations associated with the sound, etc.). The sound may correspond to a vibration associated with a change in pressure that may be audible (e.g. within a frequency of about 20 Hertz to about 20,000 Hz, a sound level from about 0 decibels to 100 decibels or more, etc.) or inaudible (e.g. low frequency sound known as infrasound; high frequency sound known as ultrasound, etc.). The sound applied may be depend upon a comfort level of a user (i.e. sound level is not so high that it becomes uncomfortable) and/or usefulness of the sound at producing therapeutic vibrations (e.g. at or near a resonance frequency associated with, for instance, therapeutic device 120, the cilia within a user's sinuses, the bones and/or cartilage of the user's sinuses, etc.). The vibration generator may provide the sound to the user at constant rate or variable rate of amplitude, frequency and/or sound pressure. For example, the sound may resemble humming (e.g. a sound at a frequency of about 100 to 150 Hz, more particularly, from about 115 to about 140 Hertz, etc.) at a range of sound levels (e.g. from about 20 decibels to about 100 decibels). The sound may vary depending upon the amount of congestion in the user, the pressure in the ears of the user, etc. The vibration generator may generate a sound that causes therapeutic device 120, or a portion thereof, to vibrate. These vibrations may be transferred to the user via seal 220 and/or nasal pillows 240. Additionally, or alternatively, sound from the vibration generator 230 may cause vibrations within the user (e.g. cilia in the user's sinuses may vibrate, the bones and cartilage of the sinuses may vibrate, mucus in the user's sinuses may vibrate, etc.).

The sound may be created from a signal generated by the vibration generator 230 when the vibration generator 230 includes a signal source. The signal source may generate one or more signals (e.g. electrical signals, etc.) that are used by the acoustic device of vibration generator 230 to generate the sound waves or patterns of sound waves described herein. The signal source may correspond to, for example, a device that may produce a sound signal (e.g. a lone generator, etc.) or a medium (e.g. a hard drive, a storage medium, etc. that may store digital or analog signals) that may store a signal and an output (e.g. a digital to analog converter, etc.) that may read the signal from the medium and deliver the signal to the acoustic device to generate the sound. The signal may be provided to acoustic device when, for instance, therapeutic device is turned on, when a user controls the user interface to turn the signal on or to modify the signal etc. Additionally, or alternatively, vibration generator 230 may receive a signal, for instance from power module 260 or an external device, that may be used by acoustic device of vibration generator 230 to generate the sound described herein. Vibration generator 230 may also include an amplifier, which may increase the strength of the signal generated and/or received by the vibration generator 230.

Nasal pillows 240 may be one or more members that fit within the nose of the user. Nasal pillows 240 may transfer vibrations to the user, such as vibrations generated by vibration generator 230, pressure module 250, etc. Additionally, or alternatively, nasal pillows 240 may form a seal (e.g. by including a seal, such as seal 220) in the nasal passages of a user to permit a treatment (e.g. a pressurized gas, medication, etc.) to be provided to the user in a chamber within the nose via nasal pillows 240. For instance, nasal pillows 240 may include one or more passageways (e.g. penetrations/tubes, etc.) (not shown) through which medication, pressurized gas, etc. may be transferred from one of the modules, described herein, to the user.

Nasal pillows 240 may include one or more ballast components that are attached to, integrated into and/or formed as part of the nasal pillows. Additionally, or alternatively, ballast components may be attached to, integrated into, and or formed as a part of another component of therapeutic device 120 associated with transferring vibrations to the user, such as seal 220 or housing 210. Ballast components may be formed by high density materials (e.g., steel, copper, lead, molybdenum, silver, gold, tungsten, platinum, high density polymers such as Ecomass®, high gravity compound ceramics, etc.). The high density materials may be ergonomically shaped to fit in, over, or around the nostrils, nose, mouth and/or face of the user. For example, and not limitation, the high density materials may form a seal (similar to seal 220 except at nasal pillows) within the nostrils of a user. The mass, inertia, and/or momentum of the ballast components may enable vibrations to be imparted to the user via the nasal interface (e.g. at the nasal pillows 240, at seal 220, housing 210, etc.). Ballast components may cause vibrations to be transferred to the user in a manner that causes the nasal and/or sinus cavities of the user to vibrate accordingly. Such vibration may stimulate the nasal and/or sinus cavities in a manner that causes the fluids, mucus, solids and/or other obstructions, within the nasal and/or sinus cavities, to be loosened, drained and/or otherwise removed from the nasal and/or sinus cavities. The vibrational forces provided to the user via ballast components as described above, may be generated by the vibration generator 230, by gas module 250 (e.g. modulated gas pressure may cause the nasal interface and/or the ballast components to vibrate in a manner that imparts the vibrational forces to the user) and or by another component and/or module of therapeutic device 120 that may generate vibrations as described herein. Nasal pillows 240 may extend from housing 210 (e.g. be connected to housing and/or ballast components associated with housing, etc.), vibration generator 230, gas module 250 (such as when gas module 250 is formed as a part of housing 210, etc.), etc. to the nostrils of user when the user uses therapeutic device 120 as described herein.

Gas module 250 may provide a gas (e.g., air, water vapor, oxygen, nitrogen, helium, helox, carbon dioxide, or a combination of gases, etc.) to a user via the nasal interface (e.g. within a chamber formed by housing 210 and seal 220, within the nostrils via nasal pillows, etc.) at a positive pressure (e.g. above ambient pressure). Gas module 250 may provide gas at different modes, such as a constant mode where a constant pressure is applied when a user inhales, exhales or both; a modulated pressure, where the pressure varies; upon request by the user, etc. Gas module 250 may be connected to (e.g. formed as a pan of, via an airtight connection, etc.) housing 210, nasal pillows 240 and/or another component of therapeutic device 120 in a way that allows pressurized gas to be administered to and/or received from the user. Gas module 250 may include to a pressure vessel that may receive, contain, and/or administer a gas at a positive pressure (e.g. above ambient pressure). For example, gas module 250 may include a reservoir that may be filled with a compressed gas that, as further discussed herein, may be regulated to provide the gas to the user at a pressure below the pressure at which the gas is stored in the reservoir. Additionally, or alternatively, gas module 250 may include a pump (e.g. an electric pump, a hand-driven pump, etc.) that may generate pressurized gas, such as compressed air, for use by the therapeutic device 120. Gas module 250 may also, or alternatively, provide pressure to the user that is created when the user exhales. For example, a user may generate a pressure by exhaling (e.g. normally exhaling, exhaling in a manner similar to blowing up a balloon, etc.) into a chamber (e.g. within housing 210, a chamber formed within nostrils by nasal pillows 240, etc.) formed by therapeutic device 120. Gas module 250 may include a valve, such as the poppet valve of housing 210, which may limit the pressure in the chamber, such as by opening to allow gas to escape the chamber. The pressure may be maintained by, for instance, seal 220 and/or nasal pillows 240. The pressure may be stored in the chamber and/or redirected to a reservoir of gas module 250 and used to provide gas pleasure to the user (such as when inhaling and/or exhaling) as described herein. Additionally, or alternatively, the gas pressure may be used to create vibrations as described herein.

Gas module 250 may include a regulator (e.g. poppet valves, pressure regulation valves, single stage diaphragm pressure regulators, two stage diaphragm pressure regulators, spring-loaded regulators etc.) to control the pressure and/or rate of flow at which a gas is applied to the user. The pressure regulators may allow gas to be applied to the user at an ideal range of pressures, for example 4-25 centimeters of water (4-25 an H2O), more ideally 4-10 cm H2O. The pressure regulator may change the pressure applied to the user. The gas module 250 may also, or alternatively, include one or more shutoff valves (e.g., gate valves, ball valves, globe valves, spring loaded shutoff valve, etc.) which may be operable (e.g. by user interface 211, etc.) to start and/or stop the How of a gas from a gas source (e.g. a source of pressurized gas) to the user.

The gas module 250 may also modulate and/or oscillate the gas pressure applied to the user. Modulating the gas pressure applied to the user may create a gas pressure pulse that travels via the nasal interface into the nasal and/or sinus cavities. The gas module may modulate the gas pressure by controlling the shape of each pressure pulse. Such modulation may include controlling a rate at which the gas pressure rises, levels off, and/or falls as a function of time. The gas module may also, or alternatively, modulate the gas pressure by controlling pulse duration, duration between pulses, frequency of pulses, following a duty cycle associated with the pulses, etc. The modulating gas pressure pulses may break up and/or loosen the fluid, mucus, solids, or other obstructions within the nasal and/or sinus cavities of the user, which may promote drainage of the mucus. To modulate the gas pressure, the gas module 250 (or some other component of therapeutic device 120) may include, for example, a solenoid which may be operable to change the path the gas travels through the gas module 250. The solenoid may change the path of the gas from a first pressure regulator, which provide gas to the nasal interface at one pressure, to a second pressure regulator, which provide gas to the nasal interface at a different pressure and/or to a non-regulated passage through the gas module (which provides the gas at the pressure it is stored/created. Additional regulators (three, four, five, etc.) may be used as well, which may include using three-position (or more) solenoids, multiple solenoids, or other ways of changing the path of the gas through the regulators. In this way, the pressure at which the gas is introduced to the user may be modulated, such as by operating a solenoid. Additionally, or alternatively, the gas module may include one or more pressure regulators which may be configured to switch, in response to an input (automatic and/or manual), between two or more pressures, or between pressure and no pressure (e.g., relative to ambient pressure), to oscillate the pressure of the gas delivered to the user. The gas module may vary the gas pressure and/or frequency of the modulation of gas pressure (e.g. based on a series of modulated pressure pulses associated with a wave form, frequency and or duty cycle, etc.) to assist with breaking up and/or loosening of the fluid, mucus, solids, and/or obstructions to promote drainage of the nasal and/or sinus cavities and/or to restore Eustachian equilibrium. Varying the pressure of the gas and/or the frequency of modulation of the gas pressure may also, or alternatively, generate a gas-induced vibration, which may lie applied to the nasal interface of the user in the same and/or similar fashion as the vibrations generated by vibration generator 230 (e.g. through nasal pillows 240, seal 220, housing 210, etc.). In this embodiment, the gas module 250 may serve as the vibration generator 230 in that the gas module 250 creates vibrations by modulating the pressure applied to the user. Modulating the pressure (or, for instance, operating a solenoid valve) may cause the nasal interface (e.g. nasal pillows, etc.) to vibrate. Additionally, or alternatively, gas pressure may be modulated and/or gas vibration may be created by a user when exhaling via the nasal interface into the gas module 250, which may use the pressure generated from the exhale to generate a pressure and/or vibration as further described herein. Accordingly, gas pressure and/or gas-induced vibration may be created and or controlled, within the therapeutic device based on the inhalation or exhalation of the user, by manual force supplied by the user (e.g., a crank, etc.), and/or automatically the therapeutic device using an external power source (electrical power, etc.).

Power module 260 may include one or more power generation and/or power supply components. For example, power module 260 may include, for instance, a battery (e.g. a conventional direct current (DC) battery, etc.), a connection to an alternating current (AC) power source, such as a wall outlet, etc. Additionally, or alternatively, power module 260 may include manually powered devices that may be used to provide treatment as further described herein. For example, and not limitation, power module 260 may include a crank (e.g. a handle attached to a shaft, etc.) that may be used by a user to provide rotational energy (e.g. by turning the handle) to vibration generator 230. Vibration generator 230 may convert the rotational energy (e.g. energy from a rotating shaft) into vibrations, which may be applied to the nasal interface of the user. Additionally, or alternatively, power module 260 may include a turbine device (not shown) that generates rotational energy when the user exhales (e.g. the user exhales into, for example, housing 210 and the exhaled breath evacuates housing 210 across blades associated with the turbine device, etc.). The rotational energy from turbine device may be provided to vibration generator 230 to produce vibrations. Additionally, or alternatively, the power module 260 may include a balloon device which may be inflated by the user (e.g. by exhaling into therapeutic device 120, etc.). Balloon device may store pressure that may be used to obtain rotational energy from, for instance, turbine device. In addition to providing power to generate vibrations, power module 260 may provide power to, for instance, the user interface 211, valve 212 and associated components of housing 210, the gas module 250, medication module 270 and/or any other components of therapeutic device 120 that require electrical, mechanical, electromechanical, hydraulic, etc. power. Power module 260 may also, or alternatively, provide a signal to vibration generator 230, which signal may be used by the vibration generator 230 to generate a sound.

Medication module 270 may provide liquid, atomized, vaporized and/or powdered medication to the gas. The medication module may be connected to therapeutic device 120 (e.g. to gas module 250, housing 210, nasal pillows 240, etc.) via an air-tight connection (e.g., a hollow tube, manifold, a tee into a line associated with the gas module, etc.). The medication module may regulate the flow and/or dosage of medication, such as with a metering device, a nozzle associated with a certain cross section, etc. The medication module may include a mixing valve, a nozzle, injector, etc., which may vaporize, atomize and/or separate the medication prior to, during, and/or after the medication is applied to the user (e.g. applied directly to the user, mixed with gas from gas module 250 before being applied to user, etc.). Additionally, or alternatively, the mixing valve may uniformly distribute the medication within the gas.

The therapeutic device 120 may also, or alternatively, provide a temperature control module (not shown) which may warm, cool or otherwise control the temperature of the gas and/or medication delivered to the user via the nasal interface. The temperature control module may be connected to the gas module and/or the medication module via an air-tight connection (e.g., a tee into a line associated with the gas module and/or medication module, etc.). The temperature control module may include a heat exchanger which may apply heat to the gas and/or the medication to raise the temperature of the medication and/or the gas entering the nasal interface. Additionally, or alternatively, the temperature control module may utilize electrical resistors, which may convert electrical energy into heat energy, and which may apply heat to the gas and/or the medication to raise the temperature of the gas and/or medication. The temperature control module may cause a portion of the exhaled gas breathed by a user to be diverted to the gas that is be conditioned to be provided to the user via the nasal interface.

The therapeutic device 120 may also, or alternatively, include a moisture control module (not shown) to provide humidified gas to the user via the nasal interface. The moisture control module may be connected to the therapeutic device via an airtight connection (e.g., a manifold, a tee in one of the lines associated with the therapeutic device, etc.). The moisture control module may combine moisture (e.g., tap water, distilled water, vapor, etc.) with the gas, medication and/or both. Increasing the moisture and/or humidity of the gas entering the nasal interface may enable the membranes within the nostrils, throat, and/or mouth to remain moist and/or to lubricate the nasal and sinus cavities of the patent. Increasing the moisture and/or humidity of the gas may also, or alternatively, break up and or loosen the fluid, mucus, solids or obstructions within the nasal and/or sinus cavities of the user, which may promote drainage of the mucus. The moisture control module may include a humidifier (e.g., evaporative humidifier, impeller humidifiers, vaporizers, atomizing nozzles, ultrasonic humidifiers, forced-air humidifiers, etc.) which may increase the humidity of the gas entering the nasal interface.

Figure 3:
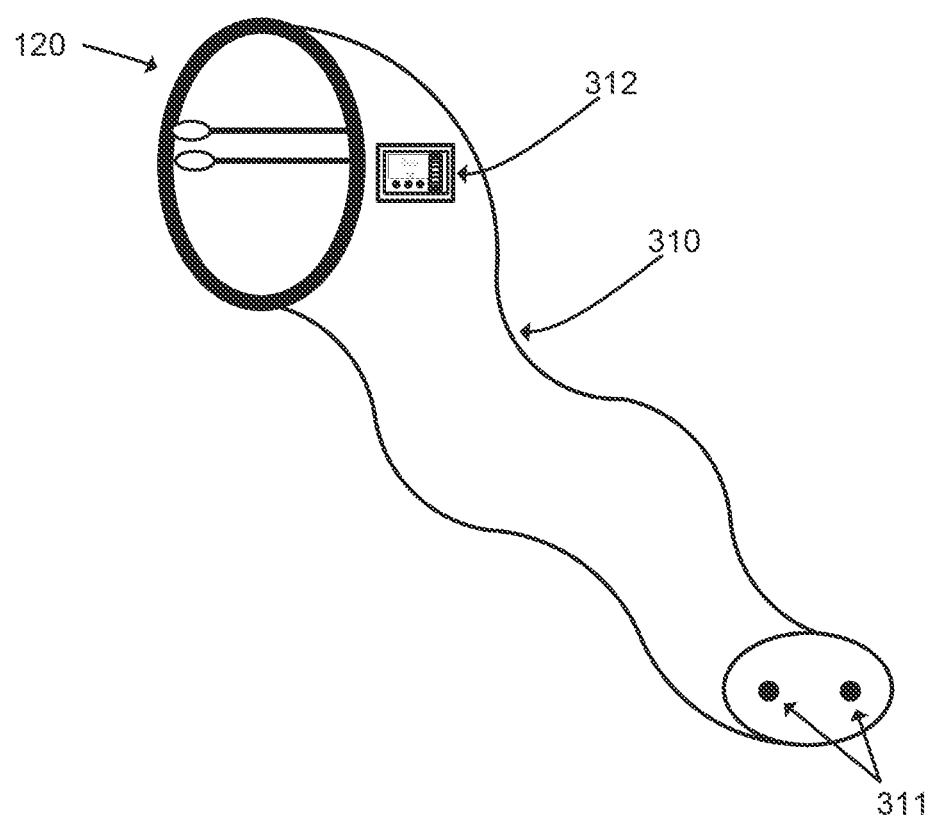
FIG. 3 depicts an alternative embodiment of the therapeutic device of FIGS. 1 & 2.

FIG. 3 depicts the therapeutic device 120 of FIGS. 1 & 2 further including a cover 310. Cover 310 may surround and/or enclose one or more components of therapeutic device 120. Cover 310 may, for instance, enclose housing 210 and the modules of therapeutic device. Cover 310 may include one or more apertures 311 which may allow a gas (e.g. gas from gas module 250, exhaled breath, air from the environment, etc.) to enter and/or exit the therapeutic device 120. In live embodiment depicted in FIG. 3, cover 310 may be designed to look like the trunk of an elephant or a child's toy (e.g. a giraffe, a superhero, etc.). Designing cover 310 in the shape of a child's toy may appeal to children who want to use therapeutic device 120. Cover 310 may also, or alternatively, include a user interface penetration 312, which may allow a user to control the therapeutic device 120 via the user interface when the cover is mounted to, placed over or otherwise installed on therapeutic device. In addition to surrounding and/or enclosing therapeutic device 120, cover 310 may also, or alternatively, reduce the noise associated with operating therapeutic device 120.

The systems and/or methods may enable the therapeutic device to administer one or more therapies to a user to treat a sinus and/or nasal condition and/or one or more symptoms associated with sinusitis (e.g., inflammation, edema, pain resulting from pressure in the sinus cavities, nasal mucus discharge, headaches, etc.) and/or to restore Eustachian equilibrium. For example, a user may position a nasal interface on, over, within, or around the nose and/or mouth of the user. In one embodiment, the nasal interface may include two nasal pillows, which may be positioned inside of the nose of the user. Additionally, or alternatively, the nasal interface may include a housing that may be placed around the nostrils and/or mouth of the user. When the user positions the nasal interface around and/or inside the nose, the nasal interface may create a seal that may maintain a pressure that may be applied to the user via the nasal interface. A chamber may be formed by applying the seal to the nasal interface of the user.

The user may operate the therapeutic device (e.g., by flipping a switch, opening a valve, pressing a button, etc.) to cause the gas module to apply a gas (e.g., air, oxygen, nitrogen, helium, helox, a combination of gasses, etc.) contained within and/or created by a gas source to the nasal interface. The gas module may include one or more pressure regulators which may regulate the gas applied to the nasal interface to be within a pressure range (e.g., 4-25 cm H20). Additionally, or alternatively, the gas module may automatically and/or by input from the user (e.g., by pressing a button, entering a preferred setting, etc. via the user interface) modulate and/or oscillate the pressure at which the gas is applied to the nasal interface and may vary the frequency at which the pressure is modulated and/or oscillated. The modulation and/or oscillation of the gas pressure applied to the user at the nasal interface may cause a gas pulse and/or gas vibration, the frequency of which may by changed (e.g., increased, decreased, or varied) by the gas module.

Gas may flow from the gas module to the nasal interface. The seal may maintain the pressure created at the nasal interface by the application of the gas by the gas module. A valve may limit the pressure created at the nasal interface and/or may prevent the pressure within a cavity from exceeding a limit (such as when the user exhales into cavity). Additionally, or alternatively, the gas module and/or the seal may maintain a specific pressure at the nasal interface when the user inhales and/or exhales. The pressure applied to the user by the gas, as well as pressure changes resulting from the modulated gas pressure and/or exhaling by the user, may break up and/or loosen mucus within the nasal and/or sinus cavities of the user, which may promote drainage of the mucus and/or may treat one or more symptoms associated with sinusitis (e.g., inflammation, edema, pain resulting from pressure in the sinus cavities, nasal mucus discharge, headaches, etc.) and/or may restore Eustachian equilibrium.

The gas module may also, or alternatively, apply a positive pressure to the nasal interface of the user by capturing pressure resulting from the exhaled breath of a user within a cavity inside of housing. The cavity may be formed when the seal is applied to the nasal interface of the user, which may create an air-tight vessel in housing. The pressure may be applied to the user only when exhaling (i.e. restricting the ability to exhale, which creates pressure, etc.) or when the exhaling and inhaling. The gas module may also, or alternatively, use the exhaled breath of the user to provide a vibration to the nasal interface of the user.

The therapeutic device may cause the nasal interface to mechanically vibrate and thereby transfer vibratory forces to the face, nose, and/or mouth, as well as the nasal and or sinus cavities of user. The user may provide input to the therapeutic device, e.g. via a user interface, to control the strength and/or rate of the vibration. Such control may enable the user to increase, decrease or maintain the vibratory forces that are imparted on the user. Mechanical vibration may be applied to the user along with and/or without the gas pressure from the gas module.

The vibration generator may include an acoustic device that may generate a sound and/or sound-driven vibration (a "sound") that causes the nasal interface and/or the user's sinuses (e.g. the user's cilia, the nasal passages, and/or bone, cartilage, etc. within the sinuses, etc.) to vibrate. The sound may be applied to the user at or near the nasal interface. The user may operate the therapeutic device, e.g. via user interface, to turn the sound on or off, to control the frequency, sound level and or sound pressure of the sound generated by the acoustic device, which may control the amount of sound and/or vibration applied to the user. Such control may enable the user to increase, decrease or maintain the vibratory forces and/or sound imparted to the user. Additionally, or alternatively, a user may operate the therapeutic device to allow a signal to be provided to the vibration generator (e.g. by connecting the therapeutic device to an external source that may provide the signal to the vibration generator, etc.). The sound may be applied at any range of frequencies, sound levels, sound pressures, etc., including sound that resembles humming (e.g. having a frequency from about 100 hertz to about 150 hertz, etc.). Acoustic vibration and/or sound may be applied to the user with and/or without gas pressure from the gas module and with and/or without treatment from other modules discussed herein.

The user may operate a medication module (e.g., by interacting with the user interface, depressing a button on medication module, etc.) of the therapeutic device to apply a medication (e.g., vaporized medications, powdered medications, etc.) to the user. The medication may break up and/or loosen mucus within the nasal and/or sinus cavities of the user, which may promote drainage of the mucus and/or may treat one or more symptoms associated with sinusitis (e.g., inflammation, edema, pain resulting from pressure in the sinus cavities, nasal mucus discharge, headaches, etc.). The medication module may apply medication to the nasal interface with or without gas from the gas module. The medication module may vaporize and/or separate medication before it is applied to the nasal interface. The medication module may uniformly mix the medication with the gas.

The user may operate a temperature module to increase and/or decrease the temperature of the gas and/or the medication applied to the user at the nasal interface. The temperature control module may apply heat to the gas, the medication, or both before it enters the nasal interface, increasing and/or decreasing the temperature of the gas and or medication may break up and/or loosen mucus within the nasal and or sinus cavities of the user, which may promote drainage of the mucus, and/or may treat one or more symptoms associated with sinusitis (e.g., inflammation, edema, pain resulting from pressure in the sinus cavities, nasal mucus discharge, headaches, etc.)

The user may operate a humidity module to increase and/or decrease the humidity of the gas, the medication or both applied to the user at the nasal interface. Increasing the humidity of the gas, the medication or both may break up and or loosen mucus within the nasal and/or sinus cavities of the user, which may promote drainage of the mucus, and/or may treat one or more symptoms associated with sinusitis.

The user may operate a power module which may provide mechanical power used to generate vibrations (e.g. via a vibration generator) to be delivered to the user via the nasal interface. The vibrations may break up and/or loosen mucus within the nasal and/or sinus cavities of the user, which may promote drainage of the mucus. Additionally, or alternatively, the vibrations may open the ear canal to relieve pressure from the ear drum, which may be created by an infection, mucus, and/or changes in pressure (e.g., taking off and/or landing in an airplane). In another embodiment, the power module may include a manually driven (e.g., by the user's breath, the user's hand, etc.) vibration device, may be shaped like a child's toy (e.g., an elephant, a giraffe, a superhero, etc.) and may be used by children to alleviate the discomfort associated with the loss of Eustachian equilibrium, such as during air travel.

FIG. 4 depicts and alternative example embodiment of the therapeutic device of FIG. 1. As shown in FIG. 4, therapeutic device 400 may include a housing 410 having a user interface 411, a valve 412, a seal 420, a vibration generator 430, a gas module 450, and a power module 460. The components illustrated in FIG. 4 are provided for explanatory purposes only, and the disclosure herein is not intended to require the components provided therein. There may be additional components, fewer components, different components, and/or differently arranged components than illustrated in FIG. 4. Also, in some implementations, one or more of the components/modules of the therapeutic device of FIG. 4 may perform one or more functions described as being performed by another one or more of the components/modules of the therapeutic device of FIG. 4.

The components of therapeutic device 400 may function the same as, or similar to, the similarly numbered components of therapeutic device 120 described in FIG. 2. For example, housing 410 may function similarly to housing 210 of FIG. 2. Housing 410 may include a user interface 411, valve 412, and lanyard 413. User interface 411 may function the same as, or similarly to, user interface 211 of FIG. 2. While user interface 411 is depicted on housing 410, user interlace 411 may be located on any one or more surfaces of therapeutic device 400. Valve 412 may function the same as, or similar to, valve 212 of FIG. 2. Lanyard 413 may provide a way for therapeutic device to connect to a user so that user does not have to hold therapeutic device 400 when using therapeutic device 400. For example, lanyard 413 may correspond to an elastic band, headband, etc. that may be placed around the head of a user 110. Tension in lanyard 413 may hold the therapeutic device 400 in place on user 110 in a way that allows a treatment to be administered to the user (e.g. may cause seal 420 to make contact with and/or form an air-tight seal around a nasal interface of a user, may cause vibrations created by therapeutic device 400 to be applied to a user, etc.). Seal 420 may function the same as, or similar to, seal 220 of FIG. 2. Vibration generator 430 may function the same as, or similar to, vibration generator 230. Gas module 450 may function the same as, or similar to, gas module 250. Power module 460 may function the same as, or similar to, power module 260.

In one particular implementation of therapeutic device 400, vibration generator 430 may be acoustically driven and may generate a sound that may be provided to the user. The vibration generator 430 may include an acoustic device that may generate the sound. The acoustic device may receive a signal from a signal source. The signal source may be included in vibration generator 430. When signal source is included in vibration generator 430, a user may vary the signal generated by signal source, such as by adjusting controls on user interface 411. Additionally, or alternatively, signal source may be included in another component of therapeutic device 400, such as power module 460, or may be an external source of electrical signals that may be converted into a sound by acoustic device of vibration generator 430. The external source may be, for instance, a signal jack (e.g. speaker jack, headphone jack, etc.) of another device (e.g. a computer, a smart phone, a tablet, an amplifier, a stereo, a signal generator, etc.) that outputs signals used to generate sounds. Power module 460 may provide electrical signals (e.g. power generator may be signal source) and/or electrical power (e.g. electrical power used by, for instance, signal source of vibration generator 430, acoustic device of vibration generator 430, an amplifier of vibration generator 430, etc.) to vibration generator 430. Power module 460 may be separate from, or formed as a part of, vibration generator 430. Alternatively, therapeutic device 400 may function without power generator 460, such as when therapeutic device 400 receives a signal from an external source.

Figure 4A:
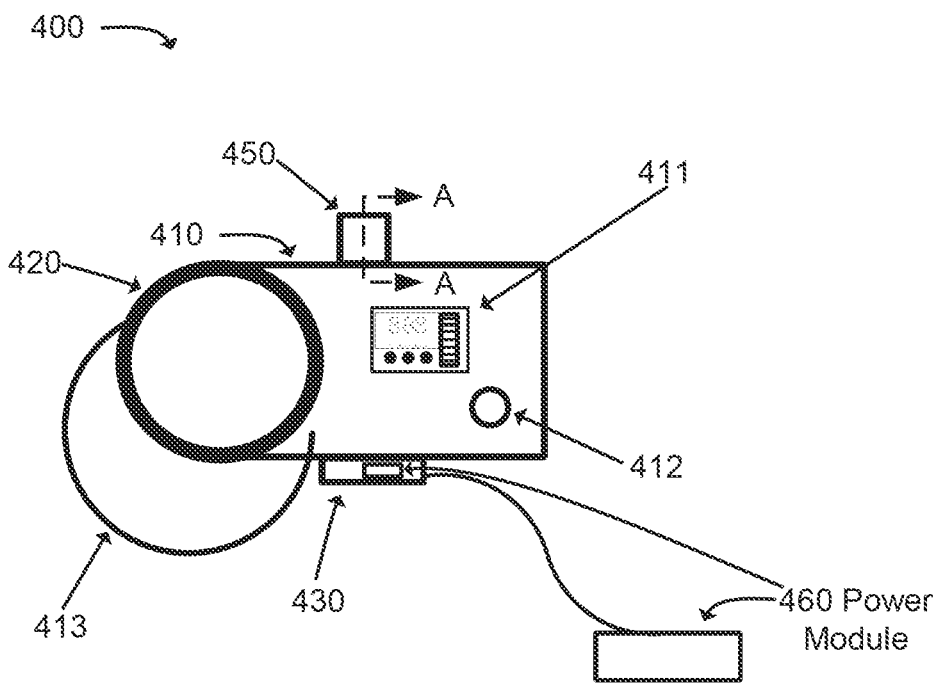
FIGS. 4A and 4B depict an alternative, non-limited example embodiment of the therapeutic device of FIG. 1.
Figure 4B:
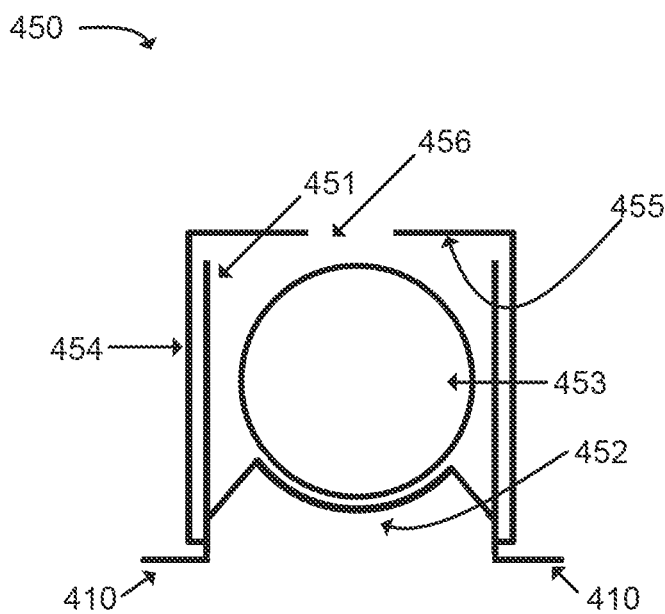

The particular implementation of therapeutic device 400 may further include gas module 450. Gas module 450 may provide a positive pressure (i.e. above ambient pressure) to the user when the user exhales and may also, or alternatively, provide a mechanical vibration to the user. Gas module 450 may be any mechanism, assembly or device that may provide a positive pressure to a user and/or a vibration to a user that is created using pressure. For example, in the embodiment depicted in FIGS. 4A and 4B, a user may place seal 420 around a nasal interface (e.g. around the nose and/or mouth, etc.) of the user to form a chamber within housing 410. The user may exhale into the therapeutic device 400 via the nasal interface to create the positive pressure within the chamber. The positive pressure may be applied to the user when the user exhales, until the user inhales and/or while the seal is applied to the nasal interface of the user. Gas module 450 may set the maximum pressure in the chamber. For instance, as shown in the embodiment of FIG. 4B, gas module 450 may include a stand 451 that extends from housing 410. Stand 451 may include a seat 452 on which a ball bearing 453 may be seated. Seat 152 may be a hollow member that includes an orifice through which the exhaled breath of the user may exit the chamber via seat 452. Valve 412 may correspond to a check valve that allows a user to inhale through the housing but that does not allow the exhaled breath of the user to escape housing 410 via valve 412.

As the user exhales, positive pressure in the chamber may generate a lift force (i.e. proportional to the pressure applied to the ball bearing 453 and the surface area of the ball bearing 453 to which the pressure is applied) that is applied the ball bearing 453 proximate the seal 452. When the lift force exceeds the weight of the ball bearing 453, the ball bearing 453 may be lifted from seat 452, thereby allowing the exhaled breath of the user to escape the chamber. The ball bearing 453 may lift from seat 452 until it contacts cap 454, particularly the upper surface 455 of cap 454, or until the lift force is less than the w eight of ball bearing 453. In this way, the weight of the ball bearing 453 may be used to set the maximum pressure of the chamber. Additionally, or alternatively, cap 454 may be adjusted to limit the distance ball bearing 453 may rise from seat 452, which may increase the maximum pressure of the chamber by limiting the amount of exhaled breath that may pass between ball bearing 453 and seat 452. Cap 454 may be adjustable, such as via a connection (e.g. threaded connection, press fit connection, etc.) between cap 454 and stand 451. Cap 454 may include a vent 456 that may be an opening that allows the exhaled breath of the user to escape gas module 450.

When the lift force is less than the weight of the ball bearing 453, the ball bearing 453 may fall back to seat 452, preventing the exhaled breath of the user from escaping the chamber of housing 410 until the lift force exceeds the weight of ball bearing 453. When ball bearing 453 falls back to seat 452, a vibration may be generated. Additionally, or alternatively, when ball bearing 453 contacts the upper surface 455 of cap 454 (e.g. as a result of the lift force), a vibration may be generated. Accordingly, as the user exhales, the ball bearing 453 may oscillate (i.e. rise and fall) to create vibrations that may be applied to the user via at the nasal interface. These vibrations may be applied to the user in addition to the positive pressure resulting from exhaling into the housing and also in addition to the vibrations applied to the user as a result of sound generated by the vibration generator 430. The positive pressure and vibrations may treat a condition of the sinuses, nasal cavities, ears, nose and/or throat.

Figure 5A:
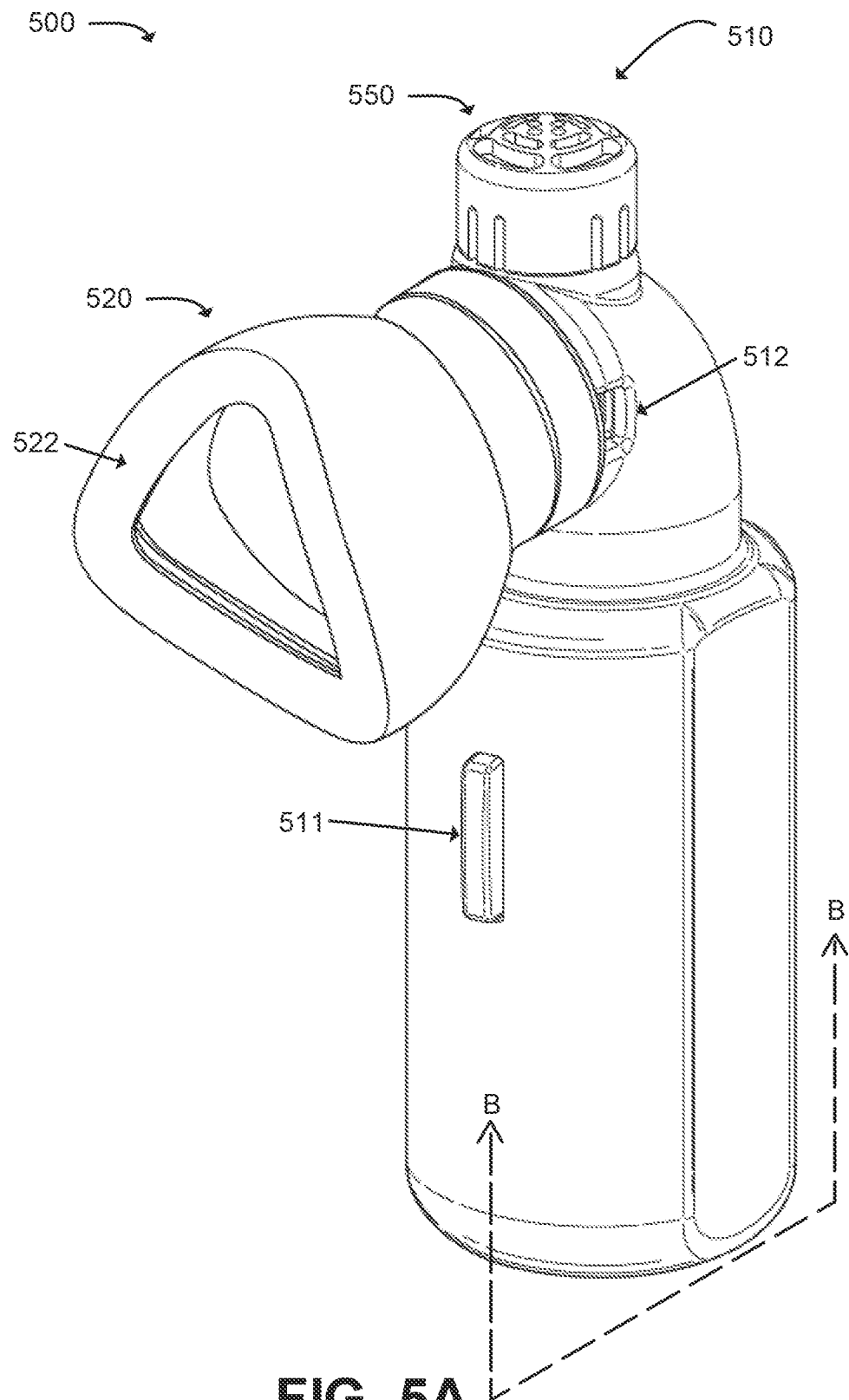
FIGS. 5A to 5E depict an alternative, non-limiting example embodiment of a therapeutic device according to the technology described herein.

FIGS. 5A through 5E depict an alternative example embodiment of therapeutic device. As shown in FIG. 5A, therapeutic device 500 may include a housing 510 having a user interface 511 and an inlet 512. Therapeutic device 500 may also include a mask 520 having a nasal interface 522. Therapeutic device 500 may also include an acoustic vibrator 530, a mechanical vibrator 550 and power supply 560. The components illustrated in FIGS. 5A through 5E are provided for explanatory purposes only, and the disclosure herein is not intended to require the components illustrated herein or to limit the embodiments anticipated herein to those illustrated herein. There may be additional components, fewer components, different components, and/or differently arranged components than illustrated in FIGS. 5A through 5E. Also, in some implementations, one or more of the components of the therapeutic device of FIGS. 5A through 5E may perform one or more functions described as being performed by another one or more of the components modules of the therapeutic device of FIGS. 5A through 5E.

The components of therapeutic device 500 may function the same as, or similar to, the similarly identified components of therapeutic device 120 and/or therapeutic device 400. For example, housing 510 may function similarly to housing 210 of FIG. 2 and/or housing 410 of FIGS. 4A and 4B, in this embodiment reflected in FIGS. 5A and 5B, housing 510 may include a user interface 511, inlet 512 (in FIG. 5B, one inlet 512, is shown, but there may be one, two, or more inlets, depending on the embodiment, and therapeutic device 500 may include a pair of inlets) connectors 513 and pivot 514. User interface 511 may allow a user to operate therapeutic device 500. User interface 511 is depicted as a button that may be depressed by a user to operate the acoustic vibration generator 530, such as by turning it on and/or off. User interface 511 may include additional elements that function the same as, or similar to, user interface 211 and/or user interface 411.

Inlet 512 may correspond to an aperature in housing 510 through which air may supplied when a user inhales. In therapeutic device 500, each inlet 512 (only one is shown) is formed from three apertures. Therapeutic device 500 includes a pair of inlets 512, one on each side of therapeutic device 500. As discussed in reference to mask 520, inlet 512 may be located at or near an area of housing 510 where mask 520 is connected to housing 510. When a user inhales while using therapeutic device 500, air may travel from the environment, through inlet 512, into mask 520 (such as through valve 526, as will be further explained herein) and to the user.

Figure 5B:
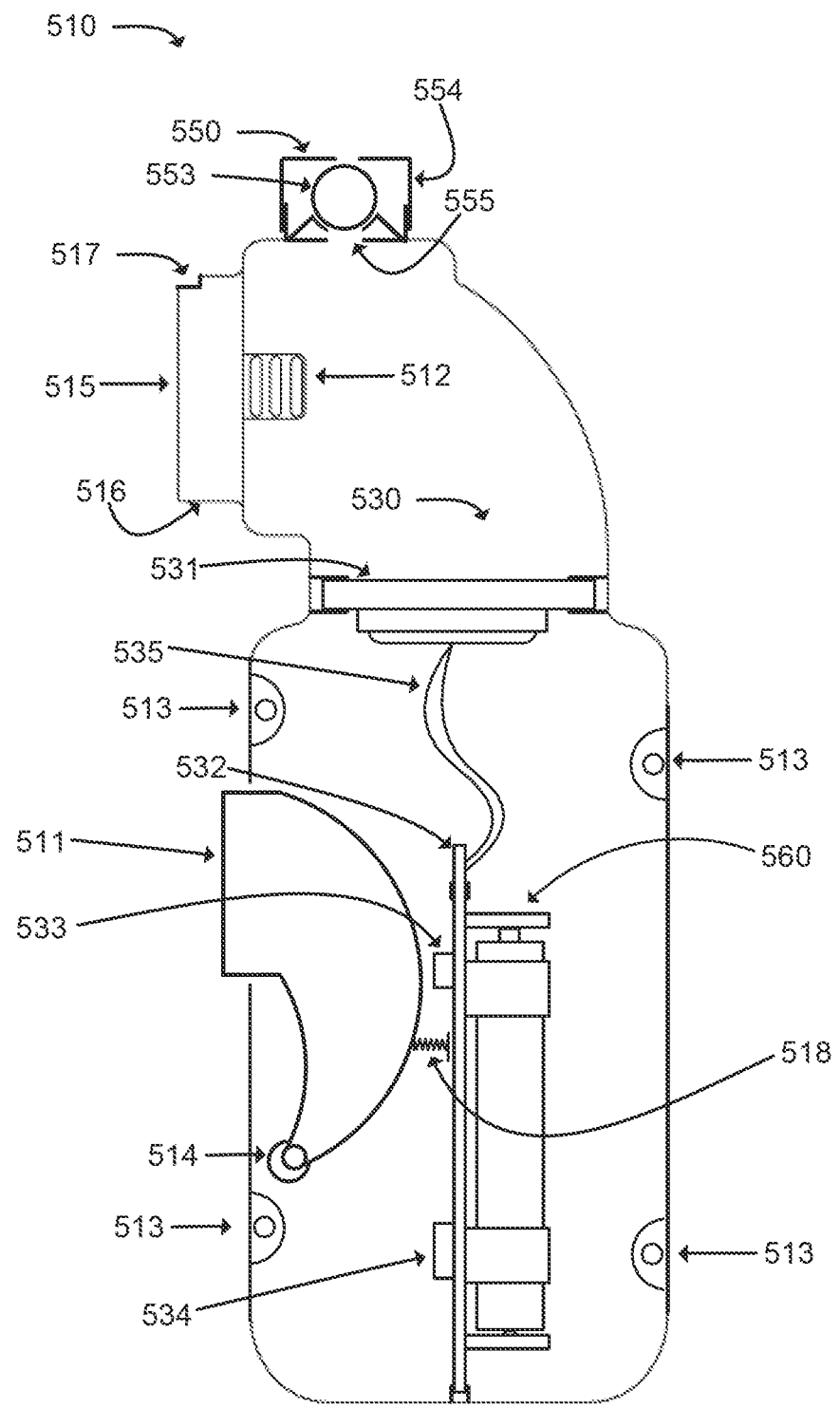

Connectors 513 may be components of housing 510 that allow housing 510 to interlock, or connect together, to form housing 510. For example, the section view of FIG. 5B is drawn along a parting line, which is where two pieces of housing 510 are joined (i.e. a right side and left side). Connectors 513 may join the two pieces of housing 510 to form housing 510. Connectors 513 may be known methods for interlocking components to join them. Pivot 514 may correspond to a section of housing 510 (such as an aperture, a hole, a spring-loaded pin connection, etc.) to which user interface 511 may be connected. In the embodiment depicted in FIG. 5B, user interface 511 may be rotatably connected to pivot 514, which may allow user interface 511 to rotate when user interface 511 is depressed by a user. Pivot 514 may provide a connection between housing 510 and user interface 511 such that user interface 511 operates therapeutic device 500 by contacting switch 533 when user interface is depressed by a user. Pivot 514 may include a spring to ensure that user interface 511 returns to an undepressed position after being depressed by a user, or, alternatively, spring 518 may be located separate from pivot 514 to serve this function.

Mask cavity 515 may correspond to an aperture (hole, opening, etc.) and a hollow cavity in housing 510 into which a portion of mask 520 may be inserted to connect mask 520 to housing 510 and/or to allow therapeutic device 500 to operate as described herein. Mask interlace 516 may correspond to a portion of housing 510 proximate mask cavity 515 that may be inserted into a portion of mask 520 to further connect mask 520 to housing 510. In the embodiment depicted in FIG. 5B, mask interface 516 is an annular shaped portion of housing 510. Mask interface 516 may include a keyway 517, which may correspond to a notch, a missing portion of material, a cutout, etc. into which a key 529 of mask 520 may be inserted to properly align mask 520 in housing 510.

Acoustic Vibrator 530 may function the same as, or similar to, vibration generator 430. Acoustic vibrator 530 may provide an acoustic vibration to a user. Acoustic vibrator may function the same as, or similar to, vibration generator 430 and may include the same and/or similar components. Acoustic vibrator 530 may include a speaker 531, circuit board 532, button 533 and amplifier 534. In the embodiment depicted in FIG. 5B, acoustic vibrator 530 may generate acoustic vibrations via speaker 531 (e.g. a speaker, tone module, buzzer, and/or any other acoustic device). Speaker 531 may receive a signal from circuit board 532 that may cause speaker 53 to produce an acoustic vibration. The acoustic vibration may correspond to a sound having a frequency of from about 100 hertz to about 150 hertz.

Circuit board 532 may include one or more components associated with providing the signal to speaker 531. Circuit board 532 may correspond to a conventional circuit board, or known substitutes. Alternatively, circuit board 532 may be omitted, and the components of circuit board may be mounted to housing 510 and/or other components of therapeutic device 500, which may be electrically connected using known methods. Circuit board 532 may include a button 533, which may be contacted by user interface 511 when a user depresses user interface 511. Button 533 may cause circuit board 532 to deliver the signal to speaker 531. Button 533 may include a delay that may cause the signal to be provided to speaker 531 for a minimum amount of time (e.g. one-half second, 1 second, 25 seconds, 1 minute, etc.) such that when button 533 is contacted by user inter face 511, the signal is provided for the minimum amount of time if user interface is released and depressed again during this minimum amount of time, the signal will not be interrupted, so speaker 531 will constantly produce the acoustic vibration. Software or hardware may control the acoustic vibration, may cause a delay, etc. Alternatively, another component of therapeutic device (e.g. a separate delay, a software routine, a loop programmed in circuit board, etc.) may provide the delay that causes the signal to be produced for the minimum amount of time. Additionally, or alternatively, therapeutic device 500 may not provide the signal for a minimum amount of time (i.e. only when button 533 is depressed). When the button is depressed, an electrical signal may be passed to a microprocessor or other component that may made decisions (i.e. allow amplifier to provide a signal, etc.) Additionally, or alternatively, user interface may cause inputs to circuit board 532 that may cause microprocessor to perform a function, (double click to provide continuous treatment, triple click for usage data, etc.)

Circuit board 532 may also, or alternatively, include amplifier 534. Amplifier 534 may produce the signal that is provided to speaker 531 (e.g. such as via leads 535, which are, for example, electric wires or other electrical connections through which the signal may be transferred) to generate the acoustic vibration. Amplifier 534 may provide a digital or analog signal to speaker. In one embodiment, amplifier 534 produces a digital signal at a rate over about 20,000 hertz, which is beyond the frequency at which humans can hear. As discussed above, the sound produced by the signal may have a frequency of from about 100 hertz to 150 hertz, more particularly about 120 hertz to about 135 hertz. Amplifier 533 may also, or alternatively, provide the signal at a rate above about 30,000 hertz. In one embodiment, amplifier 533 provides the signal at from about 30,000 hertz to about 40,000 hertz, preferably about 31,000 hertz. Providing the signal at frequencies above audible frequencies may ensure that humans, and potentially other animals, etc. cannot hear amplifier 533, the signal produced by amplifier 533 and/or fluctuations in the sound produced by speaker 531 as a result of a digital signal.

Mechanical vibrator 550 may provide a mechanical vibration to a user and/or may allow a positive pressure to be created in a chamber 523 of mask 522. Mechanical vibrator 550 function the same as, or similar to, gas module 450. As depicted, mechanical vibrator 550 may include a stand that extends from housing 510, and the stand may include a seat on which a ball bearing 553 may be seated. Seat may be a hollow member that includes an orifice 555 through which the exhaled breath of the user may exit the chamber 523. As further discussed herein, orifice 555 may align with vent 525 in mask 520 to allow the exhaled breath of the user to exit chamber 523 and go out orifice 555 via vent 525. In this way, vent 525 is aligned with ball bearing 553 to deliver the exhaled breath of the user to the ball bearing 553.

As the user exhales, positive pressure in the chamber 523 may generate a lift force at orifice 555 (i.e. proportional to the pressure applied to the ball bearing 453 and the surface area of the ball bearing 453 to which the pressure is applied) that is applied the ball bearing 553 proximate the seat. When the lift force exceeds the weight of the ball bearing 553, the ball bearing 553 may be lifted from seat, thereby allowing the exhaled breath of the user to escape the chamber. The ball bearing 553 may lift from seat until it contacts cap 554 or until the lift force is less than the w eight of ball bearing 553. In this way, the weight of the ball bearing 553 may be used to set the maximum pressure of the chamber. Additionally, or alternatively, cap 554 may be adjusted to limit the distance ball bearing 553 may rise from seat, which may increase the maximum pressure of the chamber by limiting the amount of exhaled breath that may pass between ball bearing 553 and seat. Cap 554 may be adjustable, such as via a connection (e.g. threaded connection, press fit connection, etc.) between cap 554 and stand. Cap 554 may include a vent that may be an opening that allows the exhaled breath of the user to escape mechanical vibrator 550.

When the lift force is less than the weight of the ball bearing 553, the ball bearing 553 may fall back to seat, limiting and/or preventing the exhaled breath of the user from escaping the chamber 523 until the lift force exceeds the weight of ball bearing 553. When ball bearing 553 falls back to seat, a vibration may be generated. Additionally, or alternatively, when ball bearing 553 contacts the cap 554 (e.g. as a result of the lift force), a vibration may be generated. Accordingly, as the user exhales, the ball bearing 453 may oscillate (i.e. rise and fall) to create vibrations that may be applied to the user via at the nasal interface. These vibrations may be applied to the user in addition to the positive pressure resulting from exhaling into the mask 520 and also in addition to the vibrations applied to the user as a result of sound generated by the acoustic vibrator 530. The positive pressure, mechanical vibrations and/or acoustic vibrations may treat a condition of the sinuses, nasal cavities, ears, nose and/or throat.

Power supply 560 may function the same as, or similar to, power module 260. As depicted in FIG. 5B, power supply 560 may correspond to a battery and may be connected to circuit board 532 such that power supply 560 and acoustic vibration generator 530 are located inside housing 510. Power supply 260 may provide power to acoustic vibrator 530 to allow, for instance, amplifier 533 to generate the signal and/or other components to function as described herein.

Figure 5C:
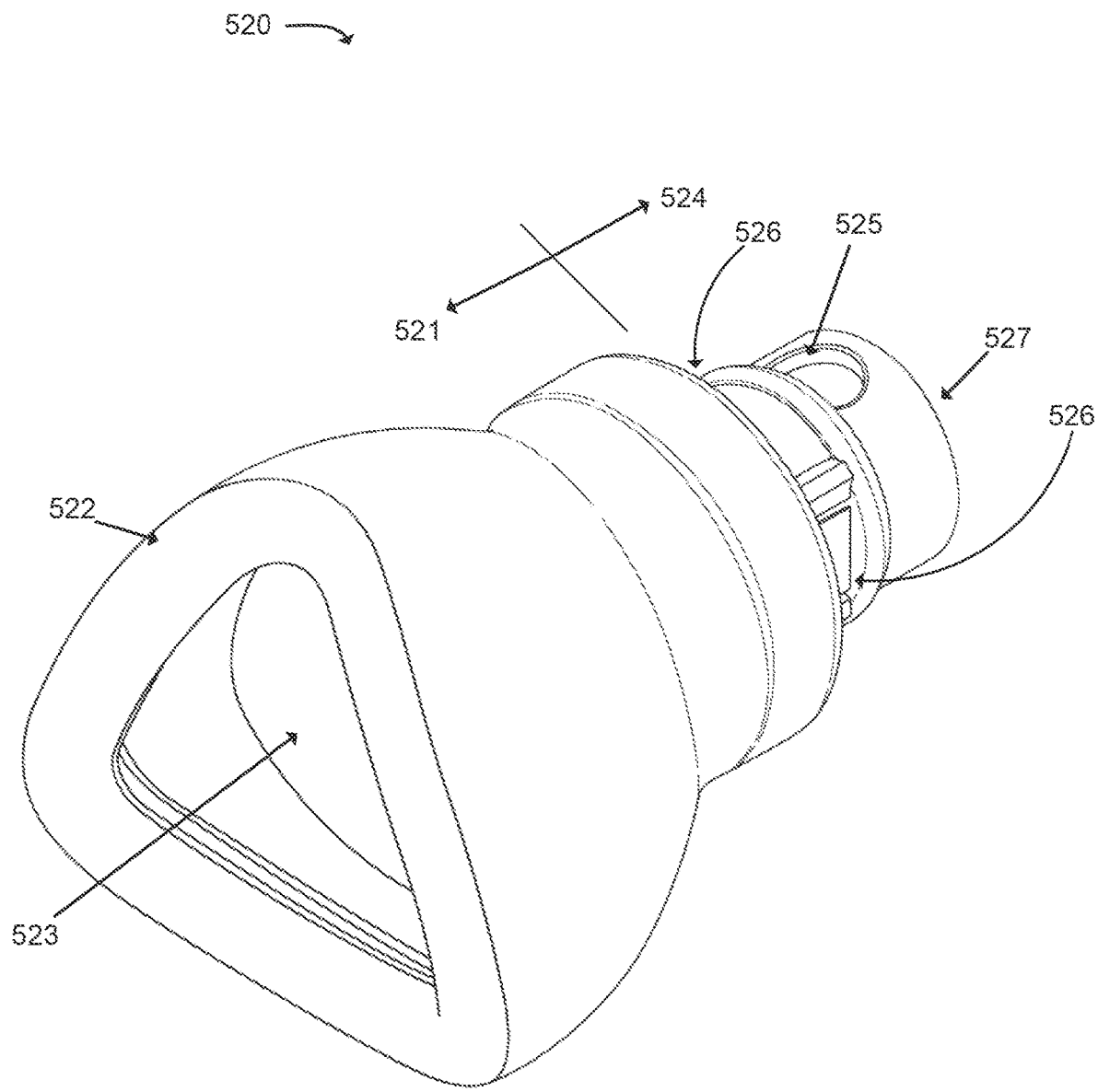

Mask 520 may correspond to a portion of therapeutic device 500 that extends from housing 510 and that may be applied around the nose of a user (i.e. is shaped to fit above the upper lip and around the nose of the user). In the embodiment depicted in FIGS. 5A through 5E, mask 520 is generally hollow-bodied so that it may be applied around the nose of a user (i.e. above the upper lip and around the nose such that both nostrils are located within mask). Applying the mask around the nose of the user (rather than the mouth or mouth and nose) may direct the vibrations (mechanical vibrations, acoustic vibrations, etc.) to the nasal passages, sinuses and/or ear canals better than when the vibrations are provided to the mouth or to a combination of the nose and mouth. In other configurations, mask may be applied to the nose and/or mouth. Mask 520 is depicted as removably connected to housing 510, which may allow a user to change the mask 520 of therapeutic device 500, such as when it becomes soiled. In other embodiments, mask 520 may be permanently connected to housing 510 and/or formed as a part of housing 510. As shown in FIG. 5C, mask 520 may include an outer portion 521 and an inner portion 524. Outer portion 521 may reside predominantly outside of housing 510 when mask 520 is connected to housing 510. Inner portion 524 may reside predominantly inside of housing 510 when mask 520 is connected to housing 510. Outer portion 521 is not limited to the components depicted in FIGS. 5A through 5E. There may additional components, fewer components, or differently arranged components titan those depicted in the figures. In other embodiments, one or more of the components of outer portion 521 may perform the functions of another one or more of the other components of outer portion 521. Further, in other embodiments certain components of outer portion 521 may be located in inner portion 524 and vice versa.

Mask 520 may be formed from any type of material. Ideally, mask 520 is formed from a material that is comfortable to a user when the user applies the nasal interface 522 around the nose. Further, mask 520 may be formed from a material that withstands the forces imparted on mask 520 by the user (i.e. pressures, forces of application to nose, etc.) and/or vibrations generated by therapeutic device 500. In one embodiment, mask 520 is a one-piece design formed from silicone. In another embodiment, mask 520 is formed from one or more plastics. In another embodiment, mask 520 is formed from multiple materials (i.e. nasal interface being formed from a softer plastic, silicone, etc., while other parts of mask 520 are formed from hard plastic, metals, etc.).

Outer portion 521 may include a nasal interface 522 and nasal chamber 523. Nasal interface 522 may be a portion of mask 522 that is applied around the nose of the user (i.e. above the upper lip and around the nose). Nasal chamber 523 may be a hollow chamber into which the nose of the user may be inserted and/or in which pressure may be maintained when nasal interlace 522 is applied to the user. When the nasal interface 522 is applied around the nose of the user, both of the users nostrils may be located inside of nasal chamber 523. Additionally, or alternatively, nasal interface 522 may form a seal with user such that pressure inside of mask 520 may be maintained, such as when a user exhales. While nasal chamber is discussed herein as being part of outer portion 521, nasal chamber 523 may be located in both inner portion 524 and outer portion 521. In the embodiment of FIGS. 5A through 5E, nasal chamber 523 extends from nasal interface 522 to diaphragm 527. In other embodiments, nasal chamber 523 may be a chamber that is differently sized, arranged, located, etc.

Inner portion 524 may include a vent 525, one or more valves 526 (therapeutic device 500 includes a pair of valves 526, one on each side, but other embodiments may include a single valve 526 or more than two valves, etc.), a diaphragm 527, a recess 528 and a key 529. Inner portion 524 is not limited to the components depicted in FIGS. 5A through 5E. There may additional components, fewer components, or differently arranged components than those depicted in the figures. In other embodiments, one or more of the components of inner portion 524 may perform the functions of another one or more of the other components of inner portion 524.

Vent 525 may correspond to an aperture that aligns with orifice 555 of mechanical vibrator 550 when mask 520 is connected to housing 510. When a user applies the nasal interface 522 around the user's nose, a seal may be formed between the user and the mask 520 such that pressure may be maintained in nasal chamber 523, the pressure may be created when a user exhales. As discussed herein, when the pressure in nasal chamber 523 is sufficient to lift ball bearing 553 from seat of mechanical vibrator 550, the exhaled breath of the user may exit the nasal chamber 523 via vent 525, which exhaled breath may operate mechanical vibrator 550 as described herein.

Valve 526 may be a check valve that allows a user to inhale through valve but that closes to maintain pressure in the nasal chamber 523, such as the pressure that is generated when a user applies the nasal interface 522 around the user's nose to form a seal and exhales into the nasal chamber 523. Valve 526 may align with inlet 512 of housing 510 so that, when a user inhales, air may travel from outside of the housing 510, through the inlet 512, through valve 526, into the nasal chamber 523 and to the user (i.e. into the nostrils of the user, allowing the user to inhale). As shown in FIG. 5E, valve 526 may be designed as a flap of material of inner portion 524 that, when the user exhales, is pressed against inlet 512 to prevent the exhaled breath of the user from escaping the nasal chamber 523 via inlet. When the user inhales, the vacuum generated by the inhale of the user draws the flap of material away from the inlet 512 (i.e. the flap is connected to the inner portion 524 at a flap end 526-P, which connection allows the flap to operate as described herein), allowing the user to inhale air via inlet 512. In this way, valve 526 opens to allow a user to breathe and closes to maintain pressure in the nasal chamber 523. Therapeutic device 500, as depicted, includes a pair of valves 526 that correspond to a pair of inlets 512.

Diaphragm 527 may correspond to a closed end of mask 520. In the embodiment depicted in FIGS. 5A through 5E, diaphragm 527 is located opposite nasal interface 522. Unlike other masks that are used in providing air or oxygen to users, such as a CPAP mask, mask 520 may not be connected to a source of oxygen/air, so mask 520 may not need a traditional opening through with the air-oxygen is provided Diaphragm 527 may be located at or near the acoustic vibrator 530 and, because diaphragm 527 is closed, diaphragm 527 may vibrate, etc., when acoustic vibrator 530 produces vibrations. Accordingly, diaphragm 527 may influence (e.g. increase and/or decrease the vibrations delivered to the user, increase and/or decrease the sound that can be heard by the user, etc.) the acoustic vibrations delivered to the user. Diaphragm 527 may be formed from a thinner material than other portions of mask 527. Alternatively, diaphragm 527 may be formed from a thicker material than other portions of mask 527. Alternatively, diaphragm 527 may not have a uniform thickness (e.g. may be thicker in the middle and thinner at the edges, etc.), which may influence the acoustic vibrations that are delivered to the user. In the embodiment depicted in FIGS. 5A through 5E, the only openings in mask 520 are nasal interlace 522, vent 525 and valve 526. Vent 525 and valves 526 are located opposite nasal interface 522, and vent 525 is located on the upper surface of inner portion 524. In this embodiment, discharge (i.e. mucus, etc.) from the user may generally stay contained in mask 520, rather than entering housing 510, which may prevent discharge from reaching acoustic vibrator 530, power supply 560, and/or other portions of therapeutic device 500.

Figure 5D:
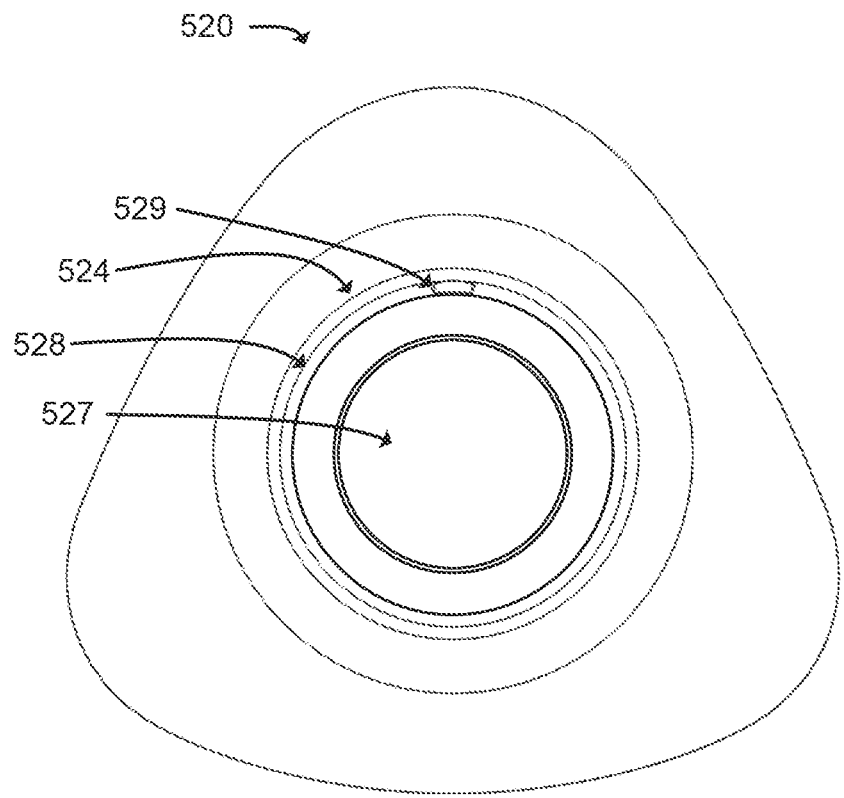
Figure 5E:
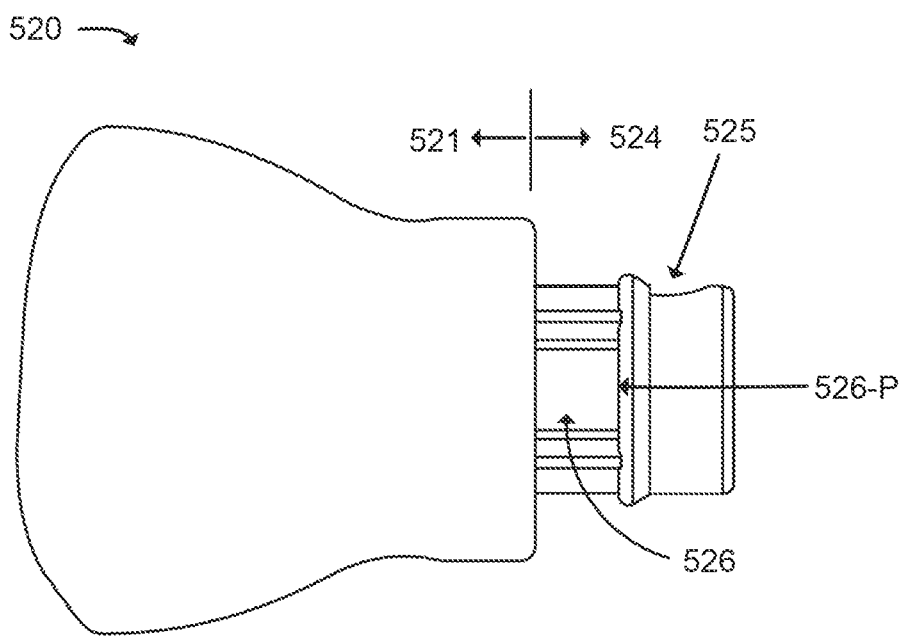

As shown in FIG. 5D, mask 520 may also include a recess 528. Mask interface 516 of housing 510 may be inserted into recess 528 to connect mask 520 to housing 510. In the embodiment depicted herein, recess 528 and mask interface 516 both have an annular shape, although any shape may be used in the design. Mask interface 516 and recess 528 may be designed so that the two may cooperate to join mask 520 and housing 510. Recess 528 may include a key 529 (e.g. a tab, a piece of material, etc.) that may align (e.g. fit within, etc.) with mask keyway 517 to properly align mask 520 in housing 510.

Figure 6A:
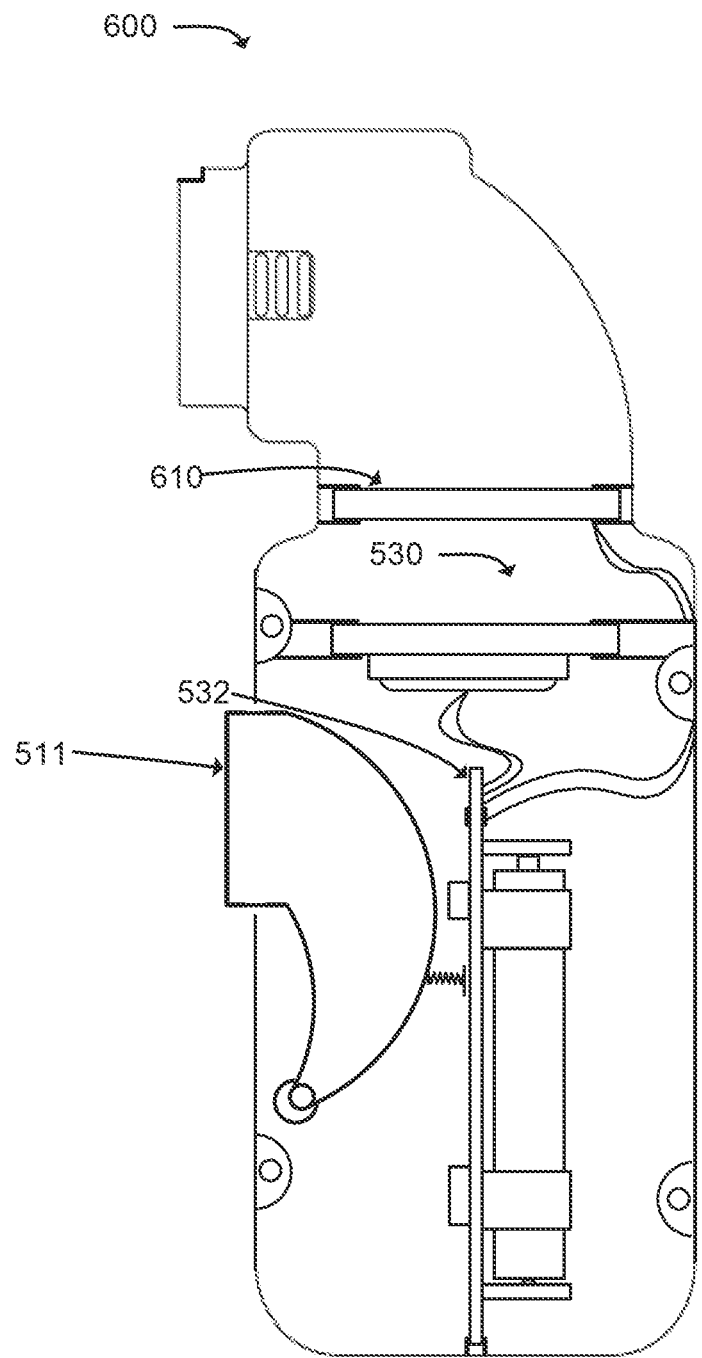
FIGS. 6A to 6C depict an alternative, now-limiting example embodiment of a therapeutic device according to the technology described herein.
Figure 6B:
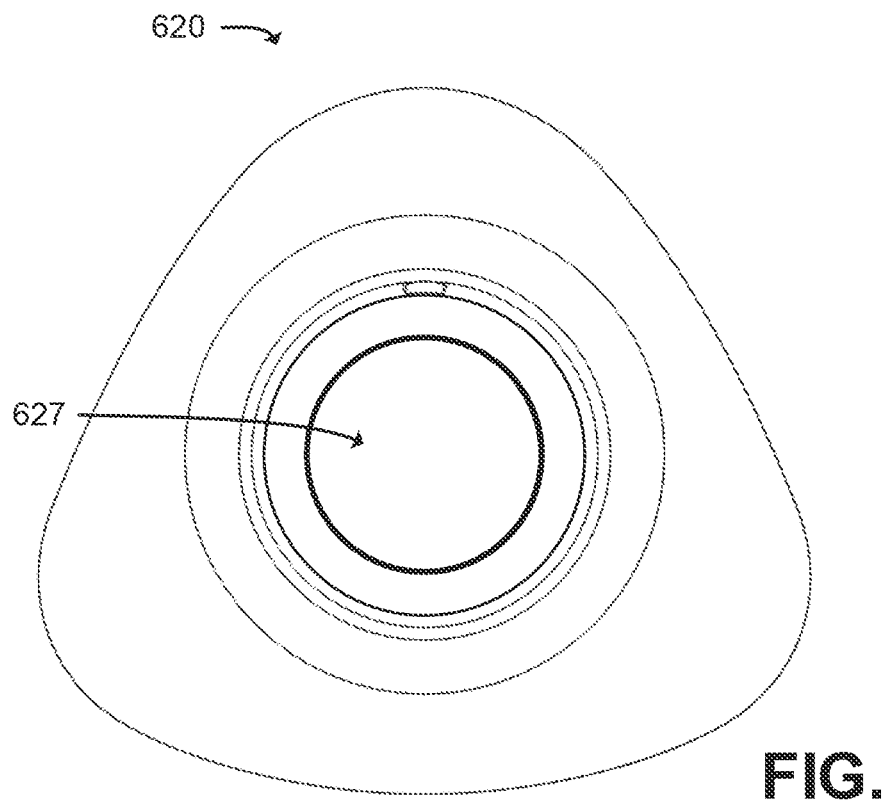
Figure 6C:
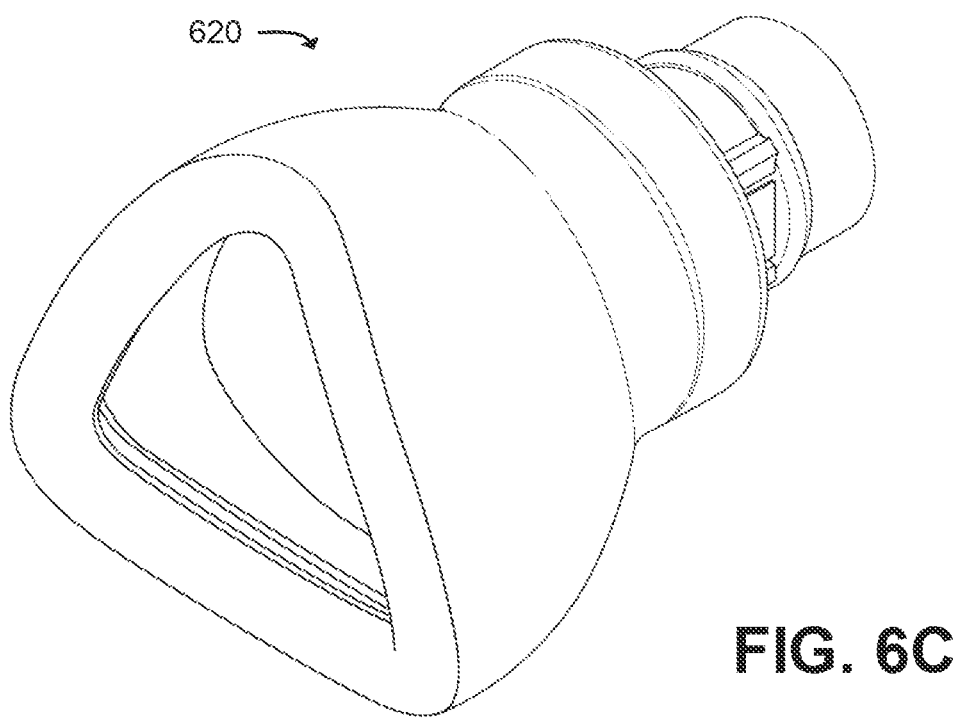

FIGS. 6A through 6C depict an alternative example embodiment of therapeutic device. As shown in FIGS. 6A through 6C, the alternative therapeutic device may be the same as, or similar to, therapeutic device 500 (and operate the same as, or similar to therapeutic device 500) except that housing 600 may be used instead of housing 510, and mask 620 may be substituted for mask 520. The components illustrated in FIGS. 6A through 6C are provided for explanatory purposes only, and the disclosure herein is not intended to require the components illustrated herein or to limit the embodiments anticipated herein to those illustrated herein. There may be additional components, fewer components, different components, and/or differently arranged components than illustrated in FIGS. 6A through 6C. Also, in some implementations, one or more of the components of the therapeutic device of FIGS. 6A through 6C may perform one or more functions described as being performed by another one or more of the components of the therapeutic device of FIGS. 6A through 6C.

The housing 600 of FIG. 6A may be the same as, or similar to, housing 510 except as explained herein. As reflected in FIG. 6A, housing 600 includes all of the components of housing 510 except that housing 600 does not include mechanical vibrator 550, or any of its components. As a result, orifice 555 is not present in housing 600 such that the exhaled breath of a user may escape housing through orifice 555. Additionally, housing 600 includes fan 610, and the position of acoustic vibrator 530 may change from that depicted with respect to housing 510 to accommodate fan 610. Fan 610 may provide positive pressure to a user by generating the pressure when fan 610 is operated. When fan 610 is operated and mask 620 is applied to a user, fan 610 forces air to the nose of the user, which creates a positive pressure. Fan 610 is connected to circuit board 532 to receive electrical power therefrom.

Fan 610 may correspond to an electrically powered fan or blower, such as a fan used to cool electrical equipment, personal fans, etc. Fan 610 may be operated by a user, such as when a user depresses user interface 511. Additionally, or alternatively, fan 610 may be operated by the circuit board 532, which may be programmed to operate fan 610 based on, for instance, the operation of acoustic vibrator 530 or other parameters set by circuit board 532.

As shown in FIGS. 6B and 6C, the mask 620 used by the therapeutic device of FIGS. 6A through 6C may the same as, or similar to, mask 520 except as provided herein. Unlike mask 520, mask 620 does not include vent 525 (as shown in FIG. 6C), as housing 600 does not include orifice 555 (or any other component of mechanical vibrator 550). Therefore, the exhaled breath of a user cannot exit mask 620 through orifice 555 or vent 525. Additionally, mask 620 does not include diaphragm 527 (as shown in FIG. 6B). Instead of diaphragm 527, mask 620 includes fan aperture 627, which corresponds to an opening or penetration in mask 620 through which a user may exhale when mask 620 is positioned around the nose of the user. Additionally, fan 610 may deliver the positive pressure it generates to the user through fan aperture 627. This causes the positive pressure generated by fan 610 to be delivered to the user when the user applies mask 620 around the user's nose and operates fan 610 to create the positive pressure, as the positive pressure is transferred through fan aperture 627. The exhaled breath of the user may increase the pressure generated by fan 610 when mask 620 is applied around the nose of the user. In that way, fan 610 operates as a positive pressure device.

FIGS. 7A through 7I depict an alternative example embodiment of therapeutic device. As shown in FIGS. 7A through 7I, the therapeutic device 700 may be the same as, or similar to, therapeutic device 500 (and operate the same as, or similar to therapeutic device 500) except that housing 701 may be substituted for housing 510. Mask 520 (not shown in FIGS. 7A through 7I) may be combined with housing 701 (i.e. in the same way that mask 520 is combined with housing 510 to create therapeutic device 500) to form therapeutic device 700. The components illustrated in FIGS. 7A through 7I are provided for explanatory purposes only, and the disclosure herein is not intended to require the components illustrated herein or to limit the embodiments anticipated herein to those illustrated herein. There may be additional components, fewer components, different components, and/or differently arranged components than illustrated in FIGS. 7A through 7I. Also, in some implementations, one or more of the components of the therapeutic device 700 may perform one or more functions described as being performed by another one or more of the components of the therapeutic device 700.

The housing 701 of therapeutic device 700 may be the same as, or similar to, housing 510 except that, instead of mechanical vibrator 550, housing 701 includes positive pressure unit 710. However, housing 701 includes orifice 555, which receives exhaled breath delivered from vent 525 of mask 520 and delivers the exhaled breath of the user to positive pressure unit 710. Positive pressure unit 710 includes many different configurations (reflected as 710A-710E) that deliver a positive pressure to a user by limiting the ability of the user to exhale through orifice 555 and vent 525, as will be further described with reference to FIGS. 7B through 7I.

Figure 7A:
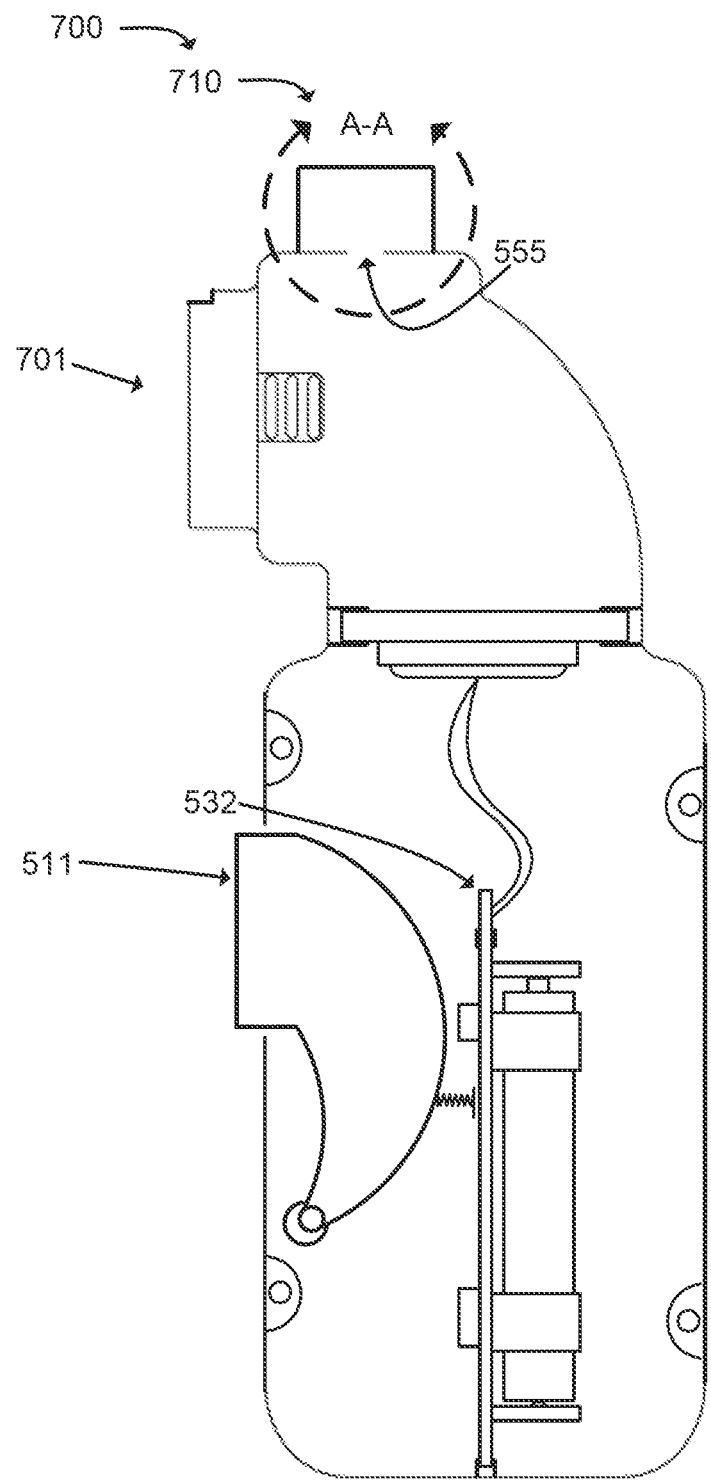
FIGS. 7A to 7I depict alternative, non-limiting example embodiments of a therapeutic device according to the technology described herein.
Figure 7B:
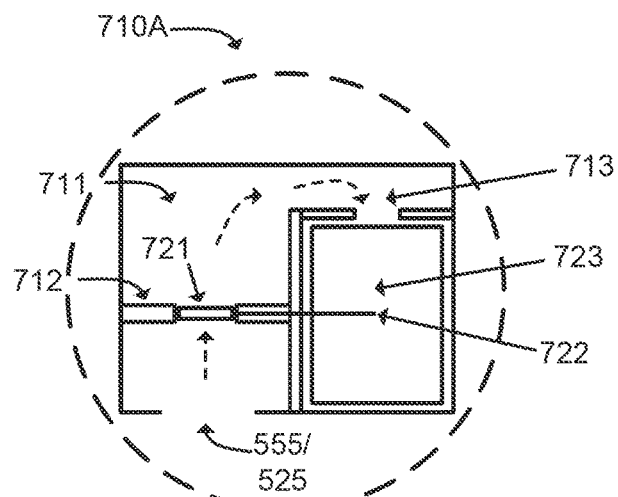
Figure 7C:
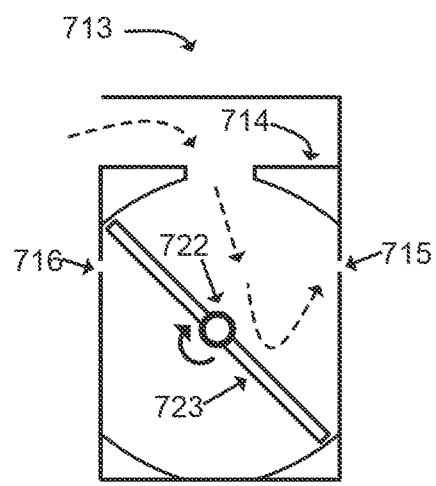
Figures 7D, 7E:
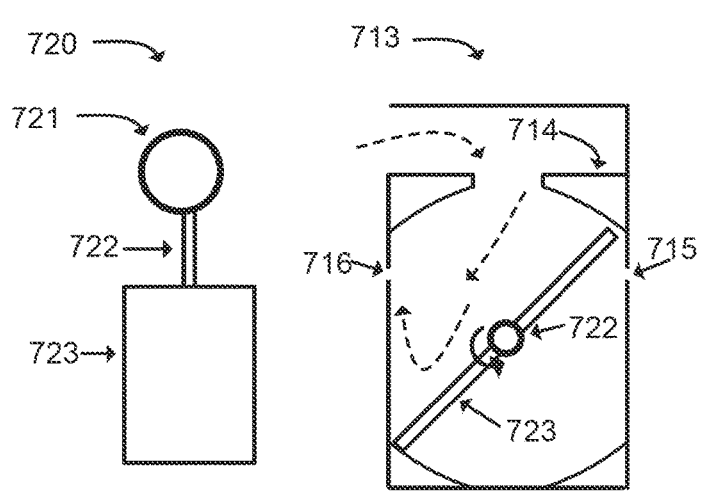

FIG. 7B through 7E reflect a first embodiment of positive pressure unit 710A. Positive pressure unit 710A includes a first chamber 711, a second chamber 713 and a modulator assembly 720. As shown in FIG. 7D, the first chamber 711 is generally parallel to the second chamber 713, and the modulator assembly 720 includes a restrictor 721 that is connected to a shaft 722. The shaft 722 is connected to a vane 723 opposite the restrictor 721. The restrictor 721 is positioned within first chamber 711 and the vane 723 is positioned within second chamber 713. The restrictor 721 has an offset connection with shaft 722 (offset from the axis of shaft 722) such that the exhaled breath of the user tends to rotate modulator assembly 720 when the exhaled breath acts on restrictor 721, which also causes the vane 723 to rotate from a first position to a second position, as will be further discussed. While not apparent from FIG. 7D, the restrictor 721 and vane 723 may be offset from each other (such as shown in FIG. 7B), such as by about 45 degrees to about 90 degrees (i.e. the orientation of rite planar faces of restrictor 721 and vane 723) in order to correctly set the first and second positions as described below. A spring or other device (not shown) may maintain the restrictor 721 in the closed position when the exhaled breath of a user is not applied to restrictor 721.

The modulator assembly 720 creates modulating pressure as described herein powered by the pressure generated by the exhaled breath of a user. As a user exhales into mask 520, the exhaled breath of the user flows into the first chamber 711 from the orifice 555 of housing 701 and vent 525 of mask 520. The restrictor 721 is located between two members 712 that prevent the exhaled breath from passing through first chamber 711. The restrictor 721 may be acted on by a spring (not shown) or other biasing element that maintains the restrictor 721 in a closed position. The pressure from the exhaled breath of the user causes the restrictor 721 to rotate (i.e. when the pressure overcomes any bias from a spring or biasing element), which opens a flow path created when restrictor 721 rotates to allow the exhaled breath of the user to pass through the first chamber 711 and into the second chamber 713, where the exhaled breath is directed in the second chamber 713 by second chamber members 714, which direct the exhaled breath toward vane 723. As the restrictor 721 rotates, the restrictor 721 is operatively connected to vane 723 via shaft 722, which causes vane 723 to also rotate. The exhaled breath then readies the second chamber 713, where the pressure acts on the vane 723, which causes the vane to rotate the opposite direction. When the restrictor 721 opens to allow the exhaled breath of the user to enter the second chamber 713, the vane may be in a first position (reflected in FIG. 7C), in which the exhaled breath can exit the second chamber 713 (and the entire therapeutic device 700) via first exit 715. As the pressure generated by the exhaled breath of the user acts on vane 723, vane rotates towards a second position (shown in FIG. 7E), which causes the restrictor to move back towards a closed position, at which point vane 723 allows the exhaled breath in the second chamber 713 to escape via first exit 715 and second exit 716 (i.e. at a midpoint between the first and second positions). Continued exhaling by the user causes the restrictor to continue to rotate back towards a more closed position until it opens to the point where the vane is m the second position (FIG. 7E), where continued exhaling causes the pressure acting on the restrictor 721 to move the vane 723 back to the first position. The process then repeats itself for as long as the exhaled breath creates sufficient pressure. In this way, the vane 723 and restrictor 721 rotate between the first position and the second position several times (i.e. in some cases, many times per second, etc.) causing the pressure in the mask to increase and decrease as the positions alternate. In this way, positive pressure unit 710A uses the exhaled breath of a user to create a modulating positive pressure that is delivered to the user at the mask.

Figure 7F:
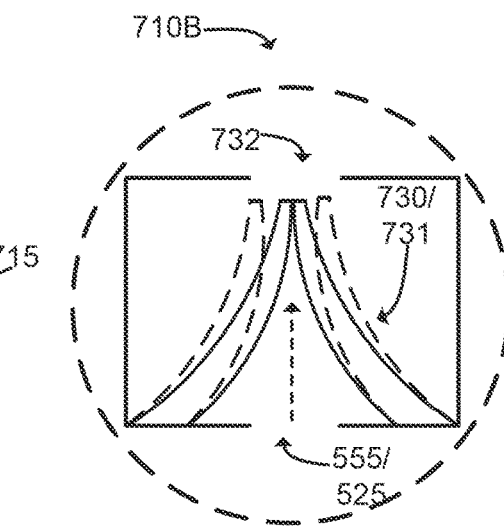

FIG. 7F reflect a second embodiment of positive pressure unit 710B. In this embodiment, positive pressure unit 710B includes a flexible nozzle 730. The flexible nozzle 730 includes a pair of nozzle members 731, which open when the exhaled breath of the user creates a sufficient pressure. In this embodiment, when the user applies mask 520 and exhales, the exhaled breath of the user enters positive pressure unit 710B via orifice 555 and vent 525. The exhaled breath acts on the nozzle members 731, which forces them outward. If the pressure generated by the exhaled breath of the user is high enough, the nozzle members 731 separate (as shown by the dashed representation in FIG. 7F), which allows the exhaled breath of the user to exit the nozzle and then exit positive pressure unit 710B through exit 732 (i.e. an opening through which the exhaled breath exits into the environment). In this way, the flexible nozzle 730 creates a positive pressure that is applied to the user. In some embodiments, the nozzle members 731 are long enough to "clap" together as the exhaled breath of the user opens the nozzle 730, which creates a whoopee cushion effect, which may vary the pressure applied to the user. In other embodiments, the nozzle members 731 are either open (when sufficient pressure is applied) or closed.

Figure 7G:
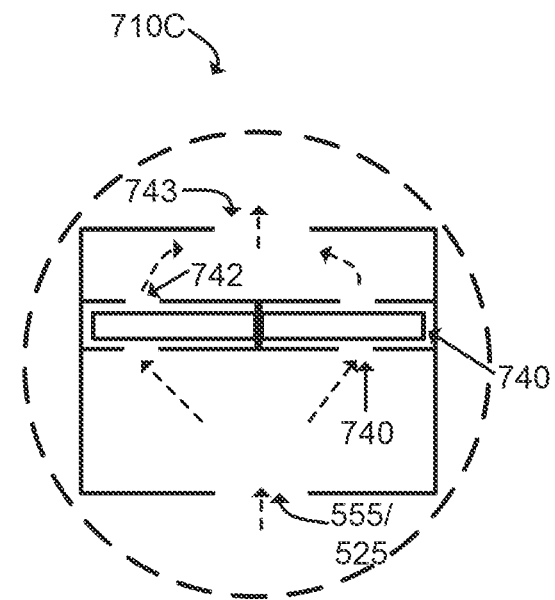

FIG. 7G reflects a third embodiment of positive pressure unit 710C. In this embodiment positive pressure unit 710C includes a fan 740 that creates a positive pressure that is delivered to the user. Fan 740 is powered by the exhaled breath of the user as described herein. When the user applies mask 520 around the nose and exhales, the exhaled breath of the user is delivered to the positive pressure unit 710 through the orifice 555 and vent 525. The exhaled breath of the user then enters the fan 740 via one or more fan openings 741, which correspond to openings (penetrations, cavities, holes, etc.) through which the exhaled breath of the user may be delivered to the blades of fan 740. The pressure delivered by the exhaled breath of the user causes the fan blades of fan 740 to rotate, which creates a positive pressure that is delivered to the user After the exhaled breath passes through the fan 740, the exhaled breath exits the fan via fan closings 742 (i.e. openings, penetrations, apertures, etc.) and then to the environment via exit 743 (another aperture or opening through which the exhaled breath may exit the therapeutic device 700). It is known that the amount of pressure delivered to the user may be determined by, for instance, the fan 740 (i.e. the type of blades, the amount of friction or resistance associated with rotating the fan blades, etc.), the size of the fan openings 741 and/or fan closings 742 and/or exit 743. Because the fan 740 must rotate for the exhaled breath of the user to escape therapeutic device 700 via exit 743, fan 740 provides a positive pressure to the user when the user applies mask 520 and exhales into therapeutic device 700.

Figure 7H:
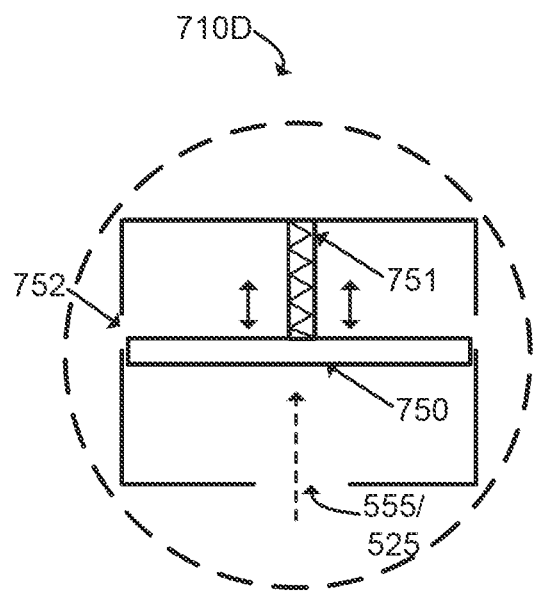

FIG. 7H reflects a fourth embodiment of positive pressure unit 710D. In this embodiment, positive pressure unit 710D includes a piston 750 that is connected to a spring 751 to deliver a positive pressure to the user. Piston 750 is acted on the pressure generated by the exhaled breath of the user, which enters positive pressure unit 710D via orifice 555 and vent 525 when the user exhales through the nose and into mask 520. When the pressure generated by the exhaled breath of the user creates a force that is strong enough to overcome the force of spring 751, piston 750 is deflected upwards, winch allows the exhaled breath of the user to be discharged from the therapeutic device 700 via one or more exits 752. When piston 750 is not deflected upwards, piston 750 may limit and/or prevent the exhaled breath of the user from reaching exit 752 or otherwise escaping the therapeutic device 700. In this way, the positive pressure unit 710D requires a positive pressure for the user to exhale, which causes a pressure to be introduced to the user of therapeutic device 700 when used.

Figure 7I:
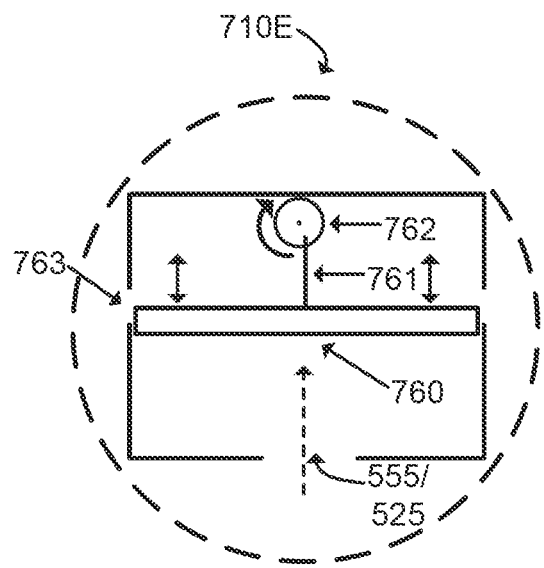

FIG. 7I reflects a fifth embodiment of positive pressure unit 710E. In this embodiment positive pressure unit 710E includes a piston 760 that is connected to a motor 762 via a shaft 761. The piston 760 may be substantially like piston 750 except it is driven by motor 762 instead of the exhaled breath of the user. Motor 762 may be an electric motor that receives power from the therapeutic device 700 (such as from a connection to circuit board 532). Motor 762 rotates, which causes shaft 761, which is connected to motor 762 at one end, to displace piston 760 within positive pressure unit 710B from an open position (not shown), in which the exhaled breath of the user may exit therapeutic device 700 through exit 763 (i.e. an opening, penetration, aperture, etc. that allows the exhaled breath to Ire discharged from therapeutic device 700), to a closed position (show in in FIG. 7I) in which the exhaled breath of the user cannot, or is limited from, exiting the therapeutic device 700 via exit 763. As a result, when the user exhales into mask 720 and motor 762 is operated to rotate such as by depressing user interface 511, etc.), the exhaled breath of the user creates a pressure when the piston 760 is in the closed positron that is released when piston 760 is in the open position. In this way, a positive pressure is delivered to the user. For clarity, in the first or closed position, the piston may restrict the exhaled breath of the user from exiting the positive pressure unit 710E and the second or open position, the piston may not restrict the exhaled breath of the user from exiting the positive pressure unit 710E. The positive pressure increases and decreases during this use, as the motor 762 rotates to move piston 760 between the open and closed positions. This pressure may relieve the conditions described herein.

The foregoing description provides illustration and description, but is not intended to be exhaustive or to limit the implementations to the precise form disclosed. Modifications and variations are possible in light of the above disclosure or may be acquired from practice of the embodiments.

It will be apparent that the apparatus, systems, methods, technologies and/or techniques, as described above, may be implemented in many different forms of hardware and/or software in the implementations described herein and illustrated in the figures. The actual or specialized hardware and/or materials used to implement the apparatus, systems, methods, technologies and/or techniques is not limited to the embodiments; it should be understood drat hardware, software and/or materials may be designed to implement the apparatus, systems, methods, technologies and/or techniques based on the description herein.

It should be emphasized that the terms "comprises"/ "comprising" when used in this specification are taken to specify the presence of stated features, integers, steps or components but does not preclude the presence or addition of one or more other features, integers, steps, components, or other groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act or instruction used in the present application should be construed as critical or essential to the embodiments unless explicitly described as such. Also, as used herein, the articles "a" and "an" are intended to include one or more items and may be used interchangeably with "one or more." Where only one item is intended, the term "one" or similar language is used. Further, the phrase "based on" is intended to mean "based, at least in part, on" unless explicitly stated otherwise.

What is claimed is:

1. A therapeutic device for treating one or more conditions associated with a user's nasal cavities, sinuses, and/or ear canals, the therapeutic device comprising:

a housing including an opening;

an acoustic vibrator that is operable to provide an acoustic vibration to the user, the acoustic vibrator located within the housing;
a fan that is operable to provide a pressure to the user, the fan located within the housing;
a power supply that provides power to the acoustic vibrator and the fan, the power supply located within the housing;
a mask that is connected to the housing proximate the opening, the mask including
 a nasal interface appliable around a nose of the user;
 a nasal chamber extending from the nasal interface, the user's nostrils being located in the nasal chamber when the nasal interface is applied around the nose of the user; and
 an aperture, the fan delivering the pressure to the user through the aperture;
whereby, the acoustic vibrator provides the acoustic vibration directly to the nose of the user when the nasal interface is applied around the nose of the user and when the acoustic vibrator is operated to provide the acoustic vibration; and
whereby, the fan provides the pressure directly to the nose of the user when the nasal interface is applied around the nose of the user and when the fan is operated to provide the pressure.

2. The therapeutic device of claim 1, where the nasal interface creates an airtight seal between the mask and the user when the nasal interface is applied around the nose of the user, the seal permitting pressure to be maintained in the nasal cavities.

3. The therapeutic device of claim 1, where the power supply is connected to a circuit board, and the circuit board operates the fan or the acoustic vibrator.

4. The therapeutic device of claim 1, where the acoustic vibration has a frequency of from 100 hertz to 150 hertz.

5. The therapeutic device of claim 1, where the mask is removably connected to the housing.

6. A therapeutic device for treating one or more conditions associated with a user's nasal cavities, sinuses, and/or ear canals, the therapeutic device comprising:
 a housing including an opening and an orifice;
 an acoustic vibrator that is operable to provide an acoustic vibration to the user, the acoustic vibrator located within the housing;
 a positive pressure unit that provides a pressure to the user that is generated by exhaled breath of the user, the positive pressure unit connected to the housing proximate the orifice such that the exhaled breath of the user enters the positive pressure unit through the orifice;
 a power supply that provides power to the acoustic vibrator, the power supply located within the housing;
 a mask that is connected to the housing at the opening, the mask including
  a nasal interface appliable around a nose of the user; and
  a nasal chamber extending from the nasal interface, the user's nostrils being located in the nasal chamber when the nasal interface is applied around the nose of the user;
whereby, the acoustic vibrator provides the acoustic vibration directly to the nose of the user when the nasal interface is applied around the nose of the user and when the acoustic vibrator is operated to provide the acoustic vibration; and
whereby, the positive pressure unit provides the pressure directly to the nose of the user when the nasal interlace is applied around the nose of the user and when the user exhales into the mask.

7. The therapeutic device of claim 6, where the positive pressure unit includes a first chamber and a second chamber, the first chamber including a restrictor and the second chamber including a vane that is connected to the restrictor via a shaft.

8. The therapeutic device of claim 7, where the restrictor has an offset connection to the shaft.

9. The therapeutic device of claim 8, where the restrictor and vane are offset by an angle of between 45 degrees and 90 degrees.

10. The therapeutic device of claim 9, where the restrictor and vane are operable from a first position to a second position.

11. The therapeutic device of claim 10, where the exhaled breath of the user exits the second chamber through a first exit and second exit when the restrictor and vane are between the first position and the second position.

12. The therapeutic device of claim 10, where the exhaled breath of the user exits the second chamber through only a first exit when the restrictor and vane are in the first position.

13. The therapeutic device of claim 6, where the positive pressure unit includes a flexible nozzle, the flexible nozzle including a pair of nozzle members.

14. The therapeutic device of claim 6, where the positive pressure unit includes a fan that is powered by the exhaled breath of the user.

15. The therapeutic device of claim 6, where the positive pressure unit includes a piston that is connected to a spring, the piston operable to an open position when the exhaled breath of the user creates a force that is stronger than a spring force generated by the spring.

16. The therapeutic device of claim 6, where the positive pressure unit includes a piston that is connected to a motor, the motor operable to move the piston from a first position, in which the exhaled breath of the user is restricted from exiting the positive pressure unit by the piston, to a second piston position, in which the exhaled breath of the user is not restricted from exiting the positive pressure unit by the piston.

17. The therapeutic device of claim 16, where the motor is connected to the power supply.

18. The therapeutic device of claim 6, where the mask is removably connected to the housing.

19. The therapeutic device of claim 6, where the mask includes a vent, the vent aligned with the orifice.

20. The therapeutic device of claim 6, where the acoustic vibration has a frequency of from 100 hertz to 150 hertz.

* * * * *